United States Patent
Roervig et al.

(10) Patent No.: US 9,901,680 B2
(45) Date of Patent: Feb. 27, 2018

(54) SPRING DRIVEN INJECTION DEVICE

(71) Applicant: Novo Nordisk A/S, Bagsvaerd (DK)

(72) Inventors: Simon Roervig, Copenhagen OE (DK); Steffen Hansen, Hilleroed (DK); Simon Munch Pedersen, Copenhagen N (DK)

(73) Assignee: Novo Nordisk A/S, Bagsvaerd (DK)

( * ) Notice: Subject to any disclaimer, the term of this patent is extended or adjusted under 35 U.S.C. 154(b) by 379 days.

(21) Appl. No.: 14/408,840

(22) PCT Filed: Jun. 25, 2013

(86) PCT No.: PCT/EP2013/063250
§ 371 (c)(1),
(2) Date: Dec. 17, 2014

(87) PCT Pub. No.: WO2014/001319
PCT Pub. Date: Jan. 3, 2014

(65) Prior Publication Data
US 2015/0202365 A1    Jul. 23, 2015

Related U.S. Application Data

(60) Provisional application No. 61/667,069, filed on Jul. 2, 2012.

(30) Foreign Application Priority Data

Jun. 29, 2012    (EP) .................................... 12174289

(51) Int. Cl.
*A61M 5/20*    (2006.01)
*A61M 5/34*    (2006.01)
(Continued)

(52) U.S. Cl.
CPC .......... *A61M 5/20* (2013.01); *A61M 5/31553* (2013.01); *A61M 5/31583* (2013.01);
(Continued)

(58) Field of Classification Search
CPC .. A61M 2005/2013; A61M 2005/2474; A61M 5/20; A61M 5/31541;
(Continued)

(56) References Cited

U.S. PATENT DOCUMENTS

| 5,092,842 | A | * | 3/1992 | Bechtold | ................. | A61M 5/20 |
| | | | | | | 604/135 |
| 5,104,380 | A | * | 4/1992 | Holman | ................. | A61M 5/20 |
| | | | | | | 604/117 |

(Continued)

FOREIGN PATENT DOCUMENTS

| EP | 338806 | 10/1989 |
| EP | 338806 A2 | 10/1989 |

(Continued)

*Primary Examiner* — Quynh-Nhu H Vu
(74) *Attorney, Agent, or Firm* — Wesley Nicolas

(57) ABSTRACT

The present invention relates to an injection device for automatic torsion spring driven injection of a liquid drug. The injection device is of the type wherein a telescopically movable needle shield activates the release of the torque of the torsion spring to drive the injection when the needle shield is moved from its extended position to a retracted position. The injection device further has a needle holder carrying the injection needle, which needle holder is axially movable both in relation to the housing and in relation to the needle shield. It is therefore possible to retract the needle shield in relation to the housing and at the same time move the needle holder to its extended position such that the injection needle is presented outside the needle shield thereby providing for easy exchange of the injection needle.

17 Claims, 16 Drawing Sheets

(51) Int. Cl.
*A61M 5/315* (2006.01)
*A61M 5/32* (2006.01)
*A61M 5/24* (2006.01)

(52) U.S. Cl.
CPC .......... *A61M 5/3257* (2013.01); *A61M 5/347* (2013.01); *A61M 5/31541* (2013.01); *A61M 2005/2013* (2013.01); *A61M 2005/2474* (2013.01)

(58) Field of Classification Search
CPC .......... A61M 5/31553; A61M 5/31583; A61M 5/3257; A61M 5/347
See application file for complete search history.

(56) References Cited

U.S. PATENT DOCUMENTS

| | | | |
|---|---|---|---|
| 7,112,187 | B2 | 9/2006 | Karlsson |
| 9,586,007 | B2 | 3/2017 | Roervig et al. |
| 2005/0261634 | A1* | 11/2005 | Karlsson ................ A61M 5/20 604/197 |
| 2006/0153693 | A1 | 7/2006 | Fiechter et al. |
| 2006/0178630 | A1 | 8/2006 | Bostrom et al. |
| 2007/0016143 | A1* | 1/2007 | Miller ................ A61M 5/3155 604/208 |
| 2008/0262436 | A1 | 10/2008 | Olson |
| 2011/0077595 | A1 | 3/2011 | Eich et al. |
| 2011/0125100 | A1* | 5/2011 | Schwirtz ............... A61M 5/002 604/198 |
| 2012/0136315 | A1* | 5/2012 | Wieselblad ............. A61M 5/20 604/189 |
| 2015/0174335 | A1 | 6/2015 | Roervig et al. |
| 2015/0202365 | A1 | 7/2015 | Roervig et al. |

FOREIGN PATENT DOCUMENTS

| | | |
|---|---|---|
| EP | 1728529 | 12/2006 |
| EP | 1728529 A1 | 12/2006 |
| EP | 2468335 A1 | 6/2012 |
| JP | H0271758 | 3/1990 |
| JP | H02502971 A | 9/1990 |
| JP | 2008515471 A | 5/2008 |
| JP | 2008541931 A | 11/2008 |
| JP | 2008541932 A | 11/2008 |
| WO | 2009/091709 A1 | 7/2009 |
| WO | 2011048223 A1 | 4/2011 |
| WO | 2011051366 A2 | 5/2011 |

* cited by examiner

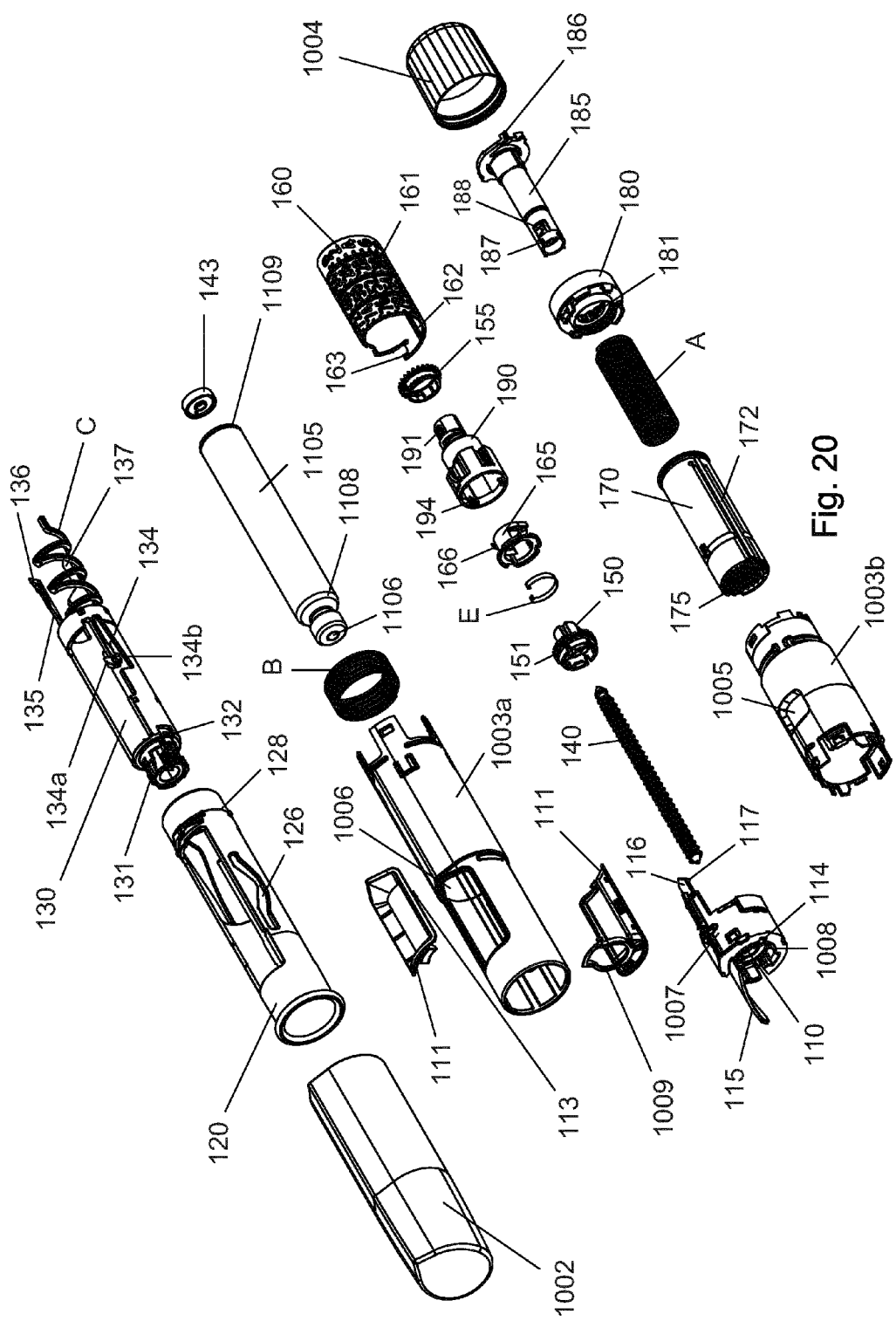

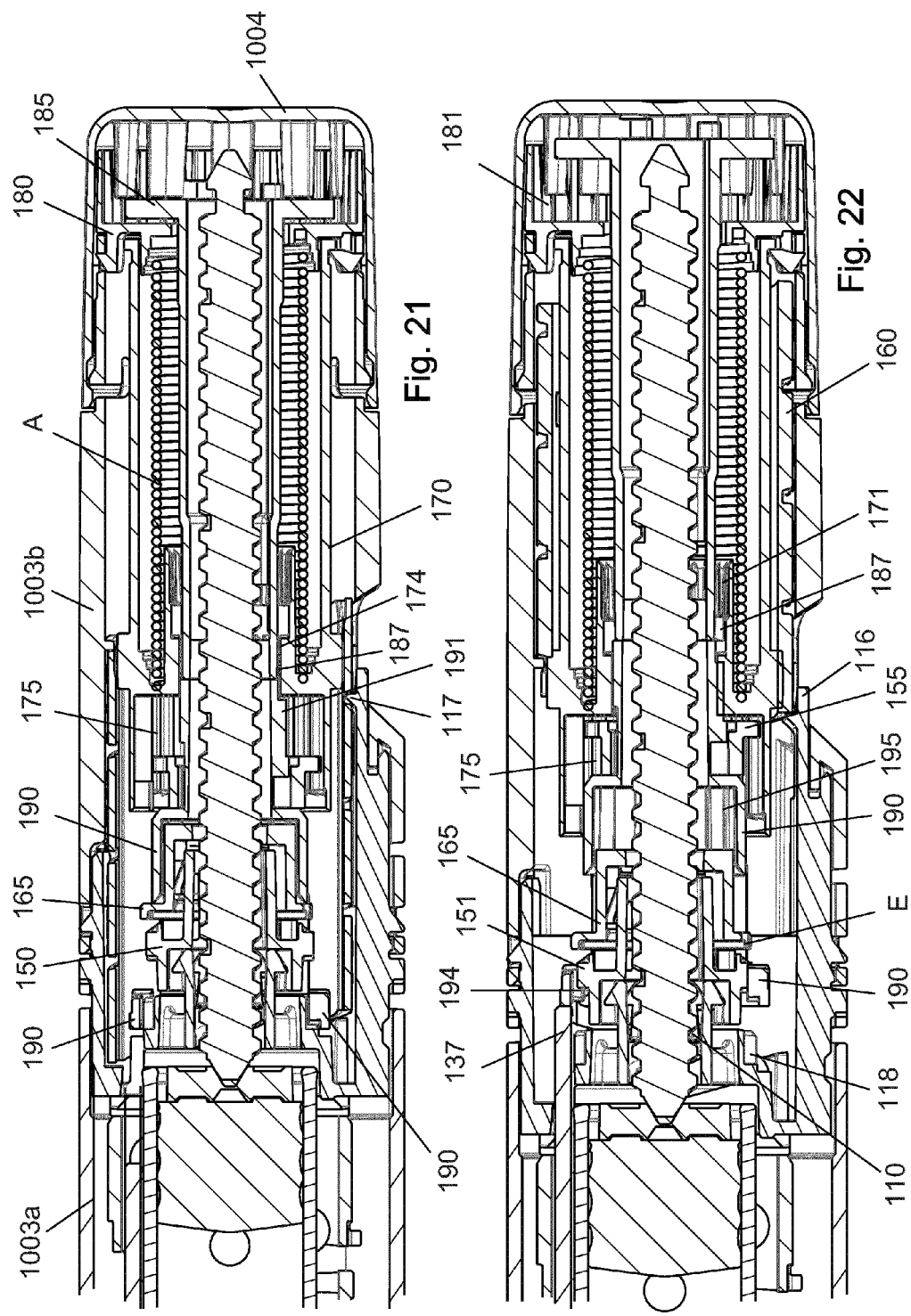

SPRING DRIVEN INJECTION DEVICE

CROSS-REFERENCE TO RELATED APPLICATIONS

This application is a 35 U.S.C. § 371 National Stage application of International Application PCT/EP2013/063250 (published as WO 2014/001319), filed Jun. 25, 2013, which claimed priority of European Patent Application 12174289.4, filed Jun. 29, 2012; this application claims priority under 35 U.S.C. § 119 of U.S. Provisional Application 61/667,069; filed Jul. 2, 2012.

THE TECHNICAL FIELD OF THE INVENTION

The invention relates to a torsion spring driven injection device for injection of multiple set doses. In particular, the invention relates to a torsion spring driven injection device of the type where the injection needle is shielded during injection and where the axial movement of the needle shield releases the injection of the set dose.

DESCRIPTION OF RELATED ART

An automatic torsion spring driven injection device is disclosed in EP 338,806. In one embodiment, the injection needle is covered by a telescopically movable needle shield. When the shield is pressed against the skin of a user, a compression spring drives the body of the pen forward such that the tip of the injection needle penetrates the skin of the user, and a torsion spring is released to perform an injection of the liquid drug contained in the injection device. In such shield triggered injection devices, the step of pressing an injection button has been eliminated and the injection needle is hidden during injection, however, exchanging the injection needle is troublesome as the user needs to remove the needle shield in order to gain access to the injection needle.

A different spring driven pen-shaped injection device having a shielded injection needle is known from U.S. Pat. No. 7,112,187. The injection device disclosed is an automatic spring-driven injection in which an actuation spring provided inside the housing thrusts the piston rod forward during injection. An important characteristic of such automatic injection device is that no element move out from the injection device during dose setting. Thus, the injection device has a constant length during operation. This particular injection device has a mode selector which is rotated to select one out of three different modes. In one mode the shield is locked and in a different mode the shield is unlocked. In the unlocked position, the shield can be moved axially between an extended and a retracted position. In the retracted position a user has access to the distal end of the injection device and is thus able to attach or remove an injection needle. Further, the mode selector can be rotated to an injection position, in which position the set dose is released when the shield is moved to its retracted position during injection.

For automatic spring driven injection devices for multiple injections of set doses in which the triggering of the injection is made by the backward movement of the needle shield a particular challenge is present. In order to exchange the injection needle, the needle shield needs to be axially removed from the hub of the injection needle such that the user can rotate or twist the hub in order to couple or decouple the injection needle. However, when performing the injection, the needle shield must trigger the release of the dose when only the distal part of the needle cannula is penetrated into the body.

In EP 338,806 this is solved by simply removing the needle shield during changing of the injection needle whereas in U.S. Pat. No. 7,112,187 it is done by a complicated mechanism involving a mode selector. However, in both examples it is difficult to explain the user how to handle the injection device as the user has to perform many different steps and remember which steps in the sequence of executing the injection he or she has fulfilled.

A further manual injection device in which the cartridge is disconnected from the injection needle by axial movement of the cartridge is described in WO 2011/051366.

DESCRIPTION OF THE INVENTION

It is an object of the present invention to provide a spring driven injection device for multiple automatic injections of set doses which are very simple to handle and which do not require any, or only very little, explanation to the user but wherein the working of the injection device is self-explanatory.

It is particularly an object of the present invention to provide a shield triggered automatic injection device which facilitates easy exchange of the injection needle without accidentally pushing on the needle shield during needle shift and thereby activating the injection process.

The invention is defined in claim 1.

Accordingly, in one aspect of the present invention, an injection device for torsion spring driven injection of a liquid drug is provided.

The torsion spring driven injection device comprises:
A housing storing all the mechanical components of the injection deivce including the cartridge containing the liquid drug. The cartridge is axially fixated to the housing, such that the cartridge cannot move axially in relation to the housing.

A dose setting arrangement for setting the size of the dose to be injected. The dose setting arrangement includes a proximally mounted dose setting button which the user rotates to set the size of the dose to be injected.

A torque spring drive mechanism for driving the set dose out from the cartridge. The drive mechanism includes a torsion spring which is strained by the user when setting a dose and released to inject the set dose. It has proven to be beneficial if a certain amount of prestraining is preloaded into the torsion spring such that small sizes of drug can be injected without the spring force necessarily having to return to zero for each individual injection. The torsion spring can alternatively be fully preloaded when the injector is delivered to the user such that the user does not need to strain the torsion spring at all. The preload is thus sufficient to empty the drug cartridge through a number of doses as in U.S. Pat. No. 7,112,187.

A torsion spring which applies its torque to rotate a piston rod guide which then during its rotation moves the piston rod axially forward to press the liquid drug out through the injection needle mounted to the injection device.

A telescopically movable needle shield for covering the distal end of the injection needle in a situation of use. The needle shield is further adapted to release at least portion of the torque of the torsion spring when moved axially, and a needle holder for carrying the injection needle.

The needle holder is slidable mounted in the housing such that the needle holder carrying the injection needle and the housing carrying the cartridge can be moved axially in relation to each other such that the proximal end of the injection needle can be moved into and out of engagement with the septum of the cartridge.

In addition, the needle shield activating the injection can be moved axially in relation to both the housing and the needle holder, whereby the needle holder carrying the injection needle can be moved to an extended position while the shield can be moved to a retracted position thus enabling easy exchange of the injection needle.

Firstly when an injection sequence is initiated, the needle holder is in its distal position extending out from the needle shield such that a user can exchange the injection needle.

When setting a dose, the needle shield is released to be moved into its extended position covering the distal end of the injection needle.

When pressed against the skin, the needle shield and the needle holder moves proximately such that the proximal end of the needle shield penetrates the septum of the cartridge where after the injection is automatically performed.

When removing the shield form the surface of the skin, the shield remains in its retracted position and the needle holder automatically slides forward such that the proximal end of injection needle decouples form the septum of the cartridge and the user can once again gain access to the injection needle.

Thus, having a housing to which the cartridge is fixed and a needle shield telescopically and axially movable in relation thereto together with a needle holder which is axial movable both in relation to the housing and to the shield provides for optimal handling of the injection needle. As explained the shield can be retracted and the needle holder pushed distally which presents the injection needle for manual handling by the user.

Also since the needle holder is axial movable, the proximal end of the needle cannula decouples instantly from the cartridge as the shield is removed from the surface of the skin, it is therefore no longer necessary to maintain the injection needle inserted into the skin of the user as no more drug will flow through the injection needle once the non-patient end is removed from the septum of the cartridge. Also when the injection needle is decoupled, air will not be sucked into the cartridge through the lumen of the injection needle why the so-called air-shot or flow-check usually performed prior to injection in order to remove air from the cartridge is no longer necessary.

The torsion spring is preferably encompassed between the housing and the piston rod guide such that the piston rod guide is able to rotate under influence of the torsion spring. However one or more other elements can be present between the housing and the piston rod guide. In one example the torsion spring might be connected to a spring base element which is secured to the housing.

Further, a rotatable drive tube for rotating the piston rod guide can be present. The drive tube can be connected to the torsion spring such that the drive tube can be rotated by the user to strain the torsion spring and released to rotate the piston rod guide. This would require a ratchet mechanism for holding the torque introduced into the torsion spring.

A clutch or activator coupling the drive tube to the piston rod guide would also be recommendable. Such clutch is movable between a first position in which the clutch is rotational locked to the housing e.g. by a toothed interface and a second position in which the clutch is rotational released from the housing and rotational coupled to both the drive tube and to the piston rod guide such that the torque of the torsion spring is transferred via the drive tube to the piston rod guide. Thus, in the first position the clutch is secured to the housing whereas the clutch in the second position is coupled to the drive tube which is released to rotate the piston rod guide.

The piston rod guide further engages the piston rod either via a keyed engagement or via a threaded engagement. In the first case the piston rod guide will rotate the piston rod distally ( in this case the piston rod is threaded to the housing). In the second case the piston rod will move distally without rotation when the piston rod guide is rotated (in this case the piston rod is keyed to the housing).

A helical compression spring is provided between the housing and the needle shield urging the needle shield in the distal direction to cover the distal end of the injection needle. However, the needle shield is engaged with the helically movable scale drum whenever the scale drum is in its zero position i.e. when no dose is set and the number "0" is displayed in the window displaying the set dose size.

This engagement is preferably made between hooks, indentations or the like on the needle shield engaging cooperating hooks or the like provided in the scale drum.

The needle shield slides on an outside surface of the needle holder. The needle holder is provided with a plurality of flexible arms extending vertically and engaging the needle shield thus preventing axial movement of the needle shield in relation to the needle holder. These arms are preferably positioned such that the arms bend inward whenever an injection needle is mounted onto the needle holder. When the arms are bended inwardly i.e. when an injection needle is mounted, the needle shield can slide freely on the needle holder. In this way the needle shield is prevented from moving into its extended position when no injection needle is mounted.

When the needle shield during injection moves from its extended position to its retracted position it moves with it the needle holder due to hook means provided on the needle shield and engaging the needle holder.

Since the needle holder carries the injection needle, the needle cannula is also moved in the proximal direction such that the proximal end of the injection needle penetrates the septum of the cartridge allowing the liquid drug in the cartridge to flow through the injection needle.

At the same time the axial and proximally movement of the needle holder activates the release of the torsion spring to drive the drive mechanism by axially moving the clutch or activator.

During the expelling of the set dose, the scale drum rotates back to its zero position. When the scale drum at the end of the injection reaches its zero position with the number "0" showing in the window, the needle holder is released from the needle shield such that the needle holder can move axially in the distal direction under influence of a spring provided between the needle holder and the housing.

In its zero position the scale drum abuts with a protrusion of the needle holder to release the needle holder from the shield such that the needle holder can slide axially in the distal direction.

In a different embodiment, the invention relates to a torsion spring driven drug delivery device of a liquid drug comprising:

A housing storing a cartridge containing the liquid drug to be injected.

A needle holder to which an injection needle can be mounted,

A needle shield for covering the injection needle during use, and wherein, the needle shield is slidable relatively to the needle holder and which needle holder is provided with a number of flexible arms preventing axial movement of the needle shield when no injection needle is mounted on the needle shield and which arms are moved into alignment with the needle holder when an injection needle is mounted on the needle holder thereby allowing the needle shield to move axially relatively to the needle holder.

In this way, the needle shield can only slide relatively to and on the needle holder when an injection needle has been mounted onto the needle holder.

When no injection needle is mounted, the needle shield is preferably secured in its proximal retracted position allowing a user to change the injection needle, and when an injection needle is mounted and the flexible arms are pressed into alignment with the needle shield, the needle shield can pass in its sliding movement towards its distal position.

However, in a further embodiment of the invention, the needle shield is either alone or in addition prevented from axial movement by engagement between the needle shield and the scale drum. In this further embodiment, the spring driven delivery device comprises:

A housing storing a cartridge containing the liquid drug to be injected.

A scale drum threadely engaged with the housing to perform an helical movement away from a zero position during setting of a dose.

A needle shield for covering the injection needle during use, which needle shield can slide axially in relation to the housing, and wherein the scale drum engages and locks the needle shield when in the zero position.

Whenever the scale drum is in its zero position, i.e. the position in which no dose has been set, and the cipher "0" appears in the window or display of the injection device, engagement means on the scale drum arrests the needle shield and secures it from axial movement.

When a user dials a dose and the scale drum moves away from its zero position, these engagement means releases and set the needle shield free to move whereby the needle shield is slidable into a position in which it covers the injection needle.

In a further embodiment of the invention, the needle shield can be biased by a compression spring to move in the distal direction when released from scale drum.

A further embodiment combines the two previous embodiments and thus requires the user to both mount an injection needle to move the flexible arms away from the needle shield and to set a dose to release the needle shield. When these two actions have been performed, the needle shield is slidable into its extended position covering the distal end of the injection needle.

DEFINITIONS

An "injection pen" is typically an injection apparatus having an oblong or elongated shape somewhat like a pen for writing. Although such pens usually have a tubular cross-section, they could easily have a different cross-section such as triangular, rectangular or square or any variation around these geometries.

The term "Needle Cannula" is used to describe the actual conduit performing the penetration of the skin during injection. A needle cannula is usually made from a metallic material such as e.g. stainless steel and connected to a hub to form a complete injection needle also often referred to as a "needle assembly" or simply an "injection needle" A needle cannula could however also be made from a polymeric material or a glass material. The hub also carries the connecting means for connecting the needle assembly to an injection apparatus and is usually moulded from a suitable thermoplastic material. The "connection means" could as examples be a luer coupling, a bayonet coupling, a threaded connection or any combination thereof e.g. a combination as described in EP 1,536,854.

Needle assemblies specially designed for pen injections systems are defined in ISO standard No. 11608, part 2, and are often referred to as "pen needles". Pen needles have a front-end for penetrating into the skin of the user and a back-end for penetrating into the cartridge containing the drug.

As used herein, the term "drug" is meant to encompass any drug-containing flowable medicine capable of being passed through a delivery means such as a hollow needle in a controlled manner, such as a liquid, solution, gel or fine suspension. Representative drugs includes pharmaceuticals such as peptides, proteins (e.g. insulin, insulin analogues and C-peptide), and hormones, biologically derived or active agents, hormonal and gene based agents, nutritional formulas and other substances in both solid (dispensed) or liquid form.

"Scale drum" is meant to be a cylinder shaped element carrying indicia indicating the size of the selected dose to the user of the injection pen. The cylinder shaped element making up the scale drum can be either solid or hollow. "Indicia" is meant to incorporate any kind of printing or otherwise provided symbols e.g. engraved or adhered symbols. These symbols are preferably, but not exclusively, Arabian numbers from "0" to "9". In a traditional injection pen configuration the indicia is viewable through a window provided in the housing. When reference is made to a "zero position" of the scale drum, this does not necessarily mean that the number "0" is present, however it merely refers to the position of the scale drum in which no dose has been set.

"Cartridge" is the term used to describe the container containing the drug. Cartridges are usually made from glass but could also be moulded from any suitable polymer. A cartridge or ampoule is preferably sealed at one end by a pierceable membrane referred to as the "septum" which can be pierced e.g. by the back-end of an injection needle. The opposite end is typically closed by a plunger or piston made from rubber or a suitable polymer. The plunger or piston can be slidable moved inside the cartridge. The space between the pierceable membrane and the movable plunger holds the drug which is pressed out as the plunger decreased the volume of the space holding the drug. However, any kind of container—rigid or flexible—can be used to contain the drug.

Since a cartridge usually has a narrower neck portion into which the rubber plunger cannot be moved, not all of the drug contained inside the cartridge can be expelled. The term "initial quantum" therefore refers to the initial quantum of the injectable content. The term "remaining content" in the same way refers to the remaining injectable content.

Further the term defines a piercing member adapted to penetrate the skin of a subject for the purpose of delivering or removing a liquid.

Using the term "Automatic" in conjunction with injection device means that, the injection device is able to perform the injection without the user of the injection device during dosing deliver the force to expel the drug. The force is typically delivered by an electric motor or by a spring as herein described which spring is strained by the user during dose setting. Such springs are usually prestrained in order to avoid problems of delivering very small doses. Alternatively, the spring can be preloaded by the manufacturer with a preload sufficient to empty the drug cartridge though a number of doses. Typically the user activates a latch or a button on the injection device to release the force accumulated in the spring when carrying out the injection.

All references, including publications, patent applications, and patents, cited herein are incorporated by reference in their entirety and to the same extent as if each reference were individually and specifically indicated to be incorporated by reference and were set forth in its entirety herein.

All headings and sub-headings are used herein for convenience only and should not be constructed as limiting the invention in any way.

The use of any and all examples, or exemplary language (e.g. such as) provided herein, is intended merely to better illuminate the invention and does not pose a limitation on the scope of the invention unless otherwise claimed. No language in the specification should be construed as indicating any non-claimed element as essential to the practice of the invention.

The citation and incorporation of patent documents herein is done for convenience only and does not reflect any view of the validity, patentability, and/or enforceability of such patent documents.

This invention includes all modifications and equivalents of the subject matter recited in the claims appended hereto as permitted by applicable law.

BRIEF DESCRIPTION OF THE DRAWINGS

The invention will be explained more fully below in connection with a preferred embodiment and with reference to the drawings in which:

FIG. 20 show an exploded view of the injection device in FIG. 19.

FIG. 21 show a cross sectional view of the injection mechanism according to the FIGS. 19-20 in the non-dosing position.

FIG. 22 show a cross sectional view of the injection mechanism according to the FIGS. 19-20 when releasing a set dose.

The figures are schematic and simplified for clarity, and they just show details, which are essential to the understanding of the invention, while other details are left out. Throughout, the same reference numerals are used for identical or corresponding parts.

DETAILED DESCRIPTION OF EMBODIMENT

When in the following terms as "upper" and "lower", "right" and "left", "horizontal" and "vertical", "clockwise" and "counter clockwise" or similar relative expressions are used, these only refer to the appended figures and not to an actual situation of use. The shown figures are schematic representations for which reason the configuration of the different structures as well as there relative dimensions are intended to serve illustrative purposes only.

In that context it may be convenient to define that the term "distal end" in the appended figures is meant to refer to the end of the injection device which usually carries the injection needle whereas the term "proximal end" is meant to refer to the opposite end pointing away from the injection needle and carrying the dose dial button as depictured in the FIGS. 1 to 6.

FIG. 1 to FIG. 7 discloses a torsion spring driven injection device during its different stages. The features and the working modes disclosed in the FIGS. 1 to 7 is common for both examples.

Figure 1:
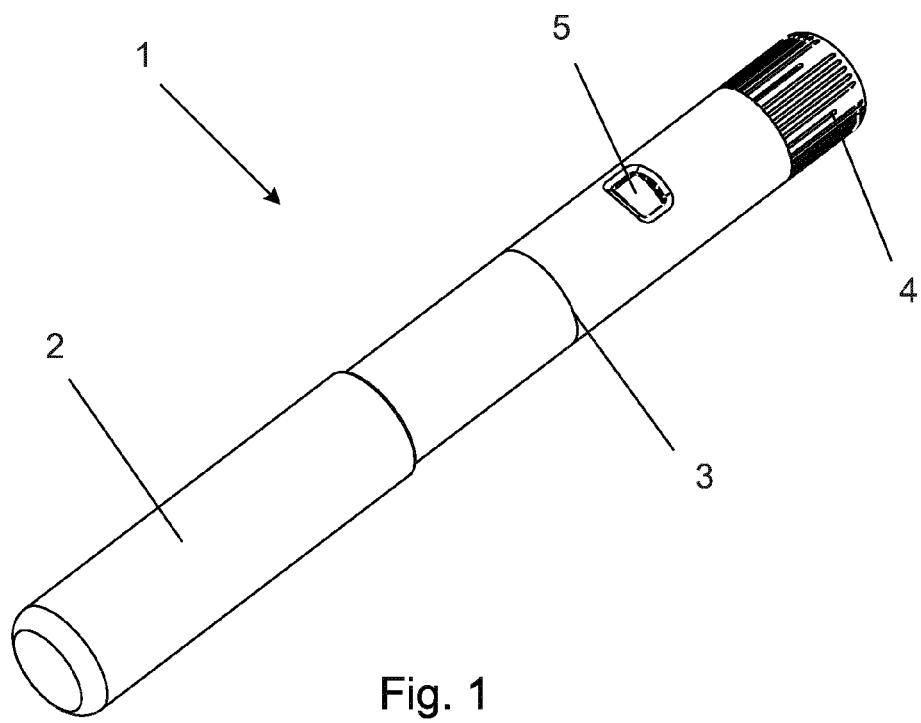
FIG. 1 show a perspective view of the injection device prior to use.

When delivered to a user, the injection device 1 has a cap 2 secured to the distal end of the housing 3 as disclosed in FIG. 1. Further, the injection device 1 has a dose setting button 4 at its proximal end and a window 5 provided in the housing 3 through which the user can visually inspect the size of the dose being set by rotating the dose setting button 4.

Figure 2:
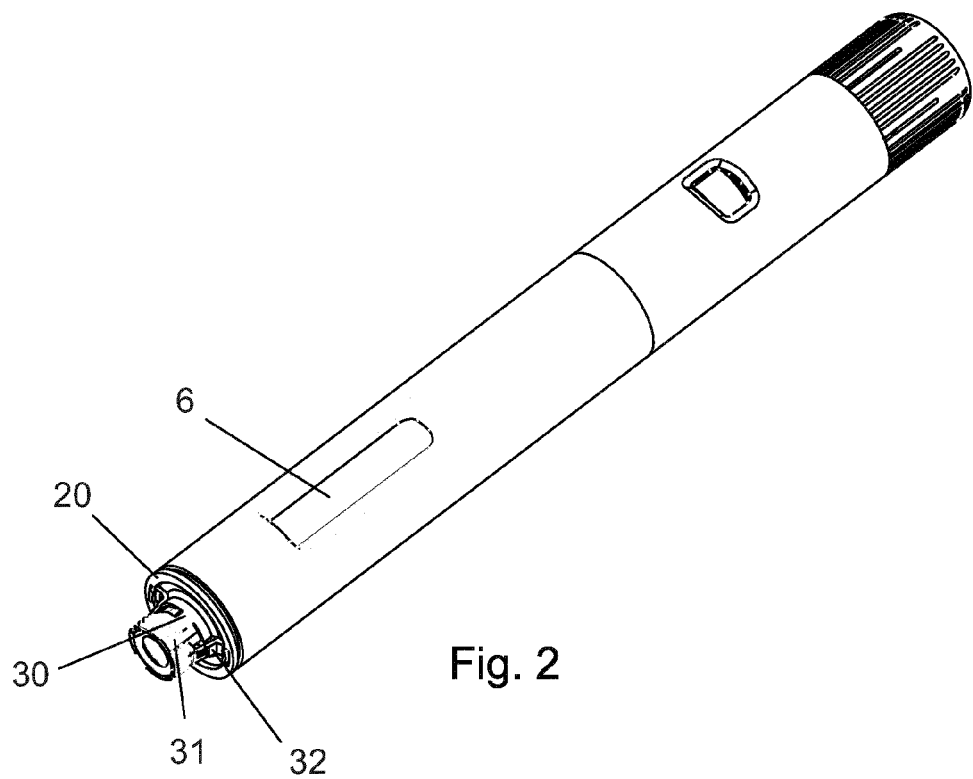
FIG. 2 show a perspective view of the injection device with the cap removed.

FIG. 2 discloses the injection device 1 with the cap 2 removed. In this mode, the user can inspect the drug contained in the injection device through the inspection opening 6. The shield 20 is in its retracted position and the user has full access to the connecting means 31 provided distally on the needle holder 30.

Figure 12:
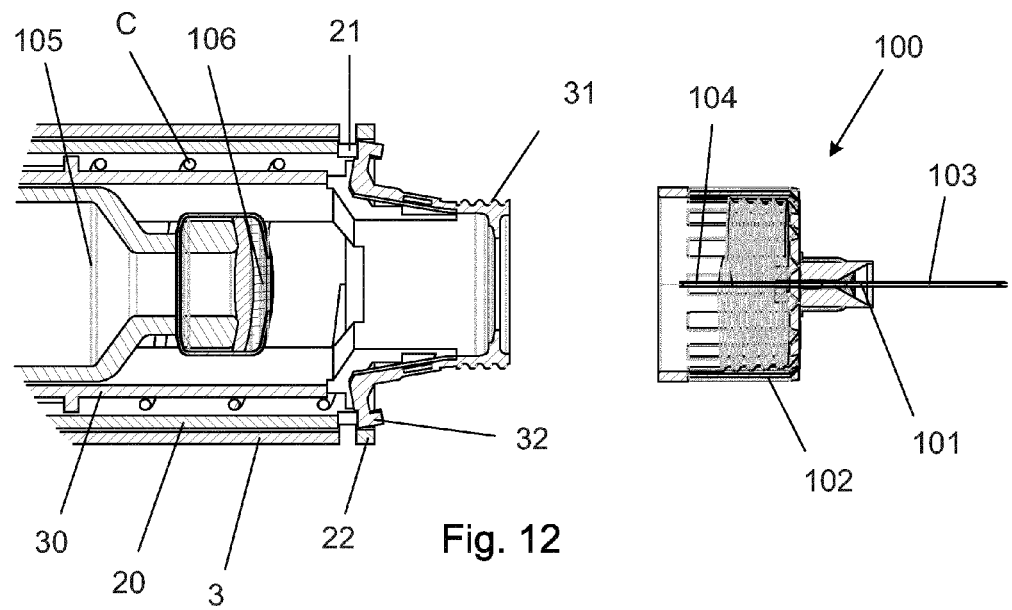
FIG. 12 show a detailed cross sectional view of the connecting means of the needle holder without an injection needle attached.
Figure 13:
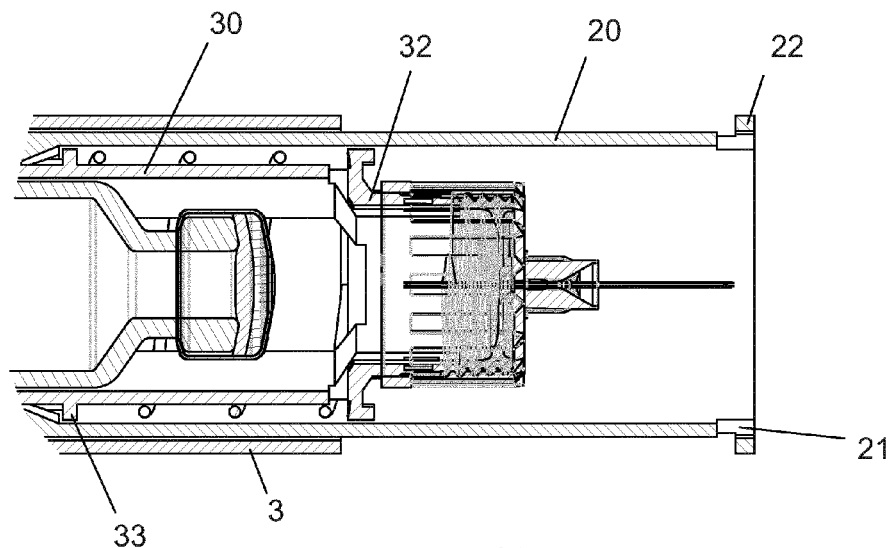
FIG. 13 show a detailed cross sectional view of the connecting means of the needle holder with an injection needle attached.
Figure 14:
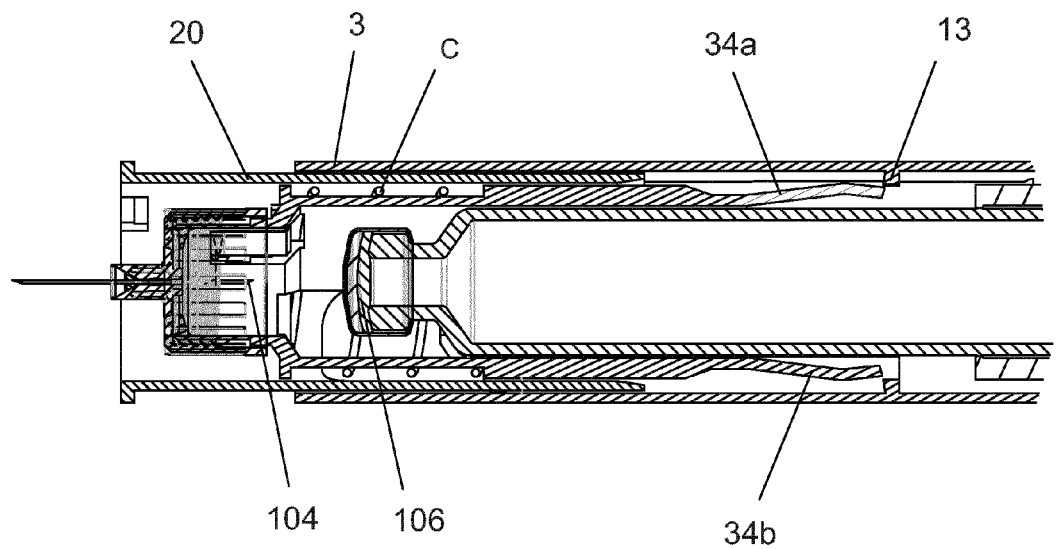
FIG. 14 show a detailed cross sectional view of the activation mechanism during injection.

In this mode the axial movement of the shield 20 in the distal direction is hindered by two flexible arms 32 provided on the needle holder 30 and shown in details on FIG. 12-13. These flexible arms 32 are provided in conjunction with the connecting means 31 such that once an injection needle 100 is connected to the connection means 31, this injection needle 100 pushes the flexible arms 32 inwardly to allow passage of the axial movable shield 20 in the distal direction.

Figure 3:
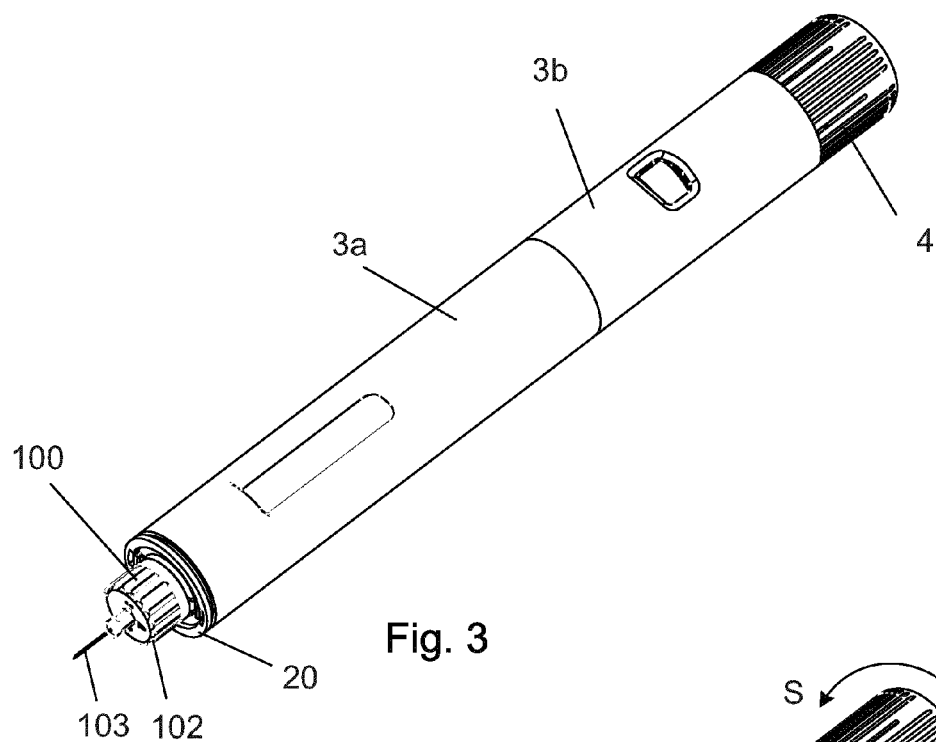
FIG. 3 show a perspective view of the injection device with the injection needle mounted.

In FIG. 3, the user has attached an injection needle 100 to the connecting means 31. The injection needle 100 is a conventional pen needle 100 (see FIG. 12) comprising a hub 102 to which a metallic needle cannula 101 is secured. The needle cannula 101 has a distal end 103 for penetrating the skin of a user and a proximal end 104 for entering into a cartridge 105 contained in the injection device 1.

Figure 4:
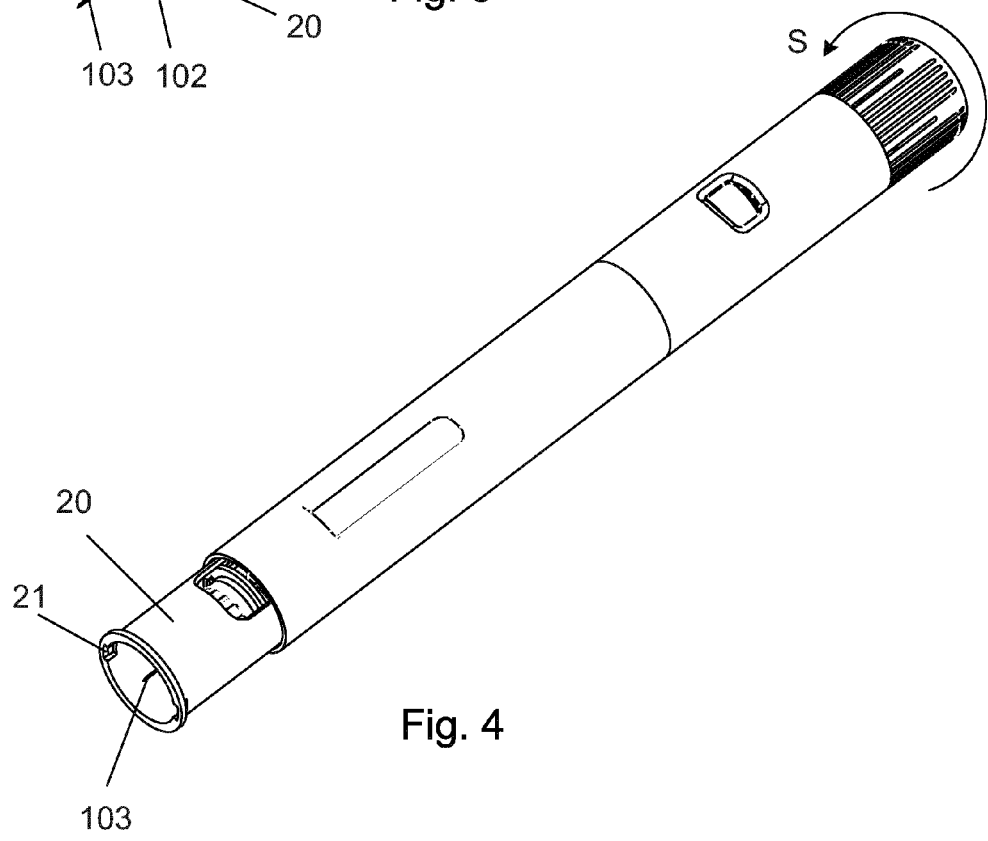
FIG. 4 show a perspective view of the injection device with the needle shield in its extended position.

When a user dials a dose by rotating the dose setting button 4 (indicated by the arrow S in FIG. 4), the shield 20 is automatically moved into its extended position as disclosed in FIG. 4. In this extended position the shield 20 visually covers the distal end 103 of the needle cannula 101, at least when the injection device 1 is viewed radially i.e. when vied from the side.

An injection is hereafter performed simply by pressing the distal end of the shield 20 softly against the skin of the user. This is indicated with the arrow I in FIG. 5. The distal part 103 of the needle cannula 101 penetrates through the skin of the user, and the shield 20 when moving into its retracted position automatically activates the injection of the set dose as will be explained later.

Figure 6:
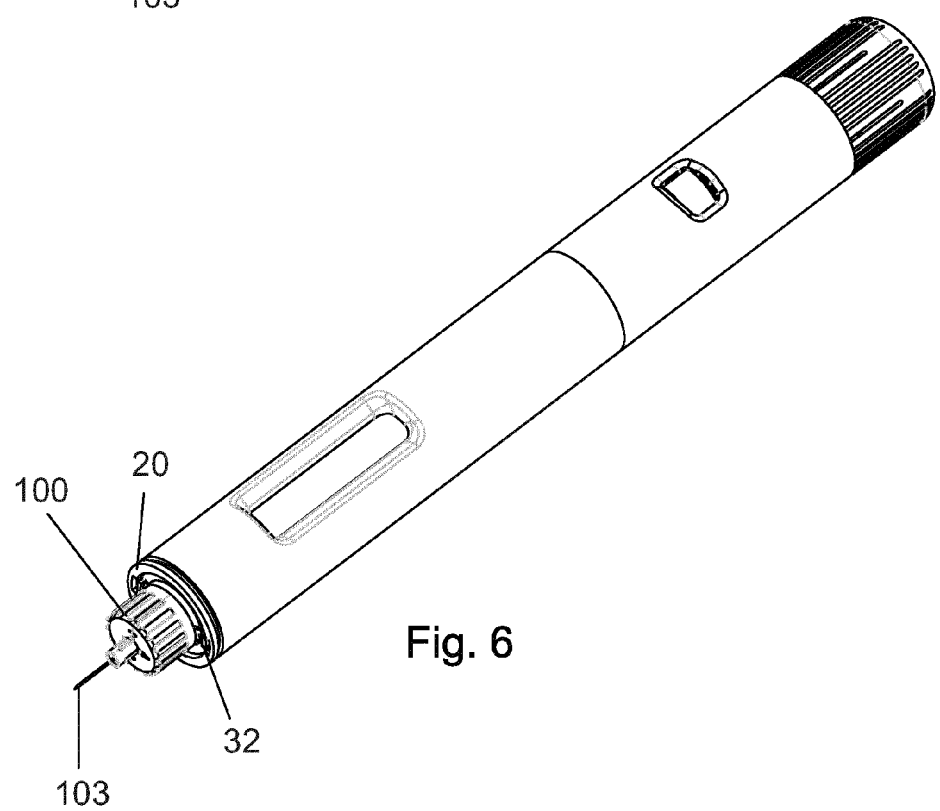
FIG. 6 show a perspective view of the injection following injection.

Following injection, when the distal end 103 of the needle cannula 101 is removed from the skin of the user as disclosed in FIG. 6, the shield 20 is maintained in its retracted position and the needle holder 30 moves axially into its extended position making it possible for the user to exchange the injection needle 100.

Figure 7:
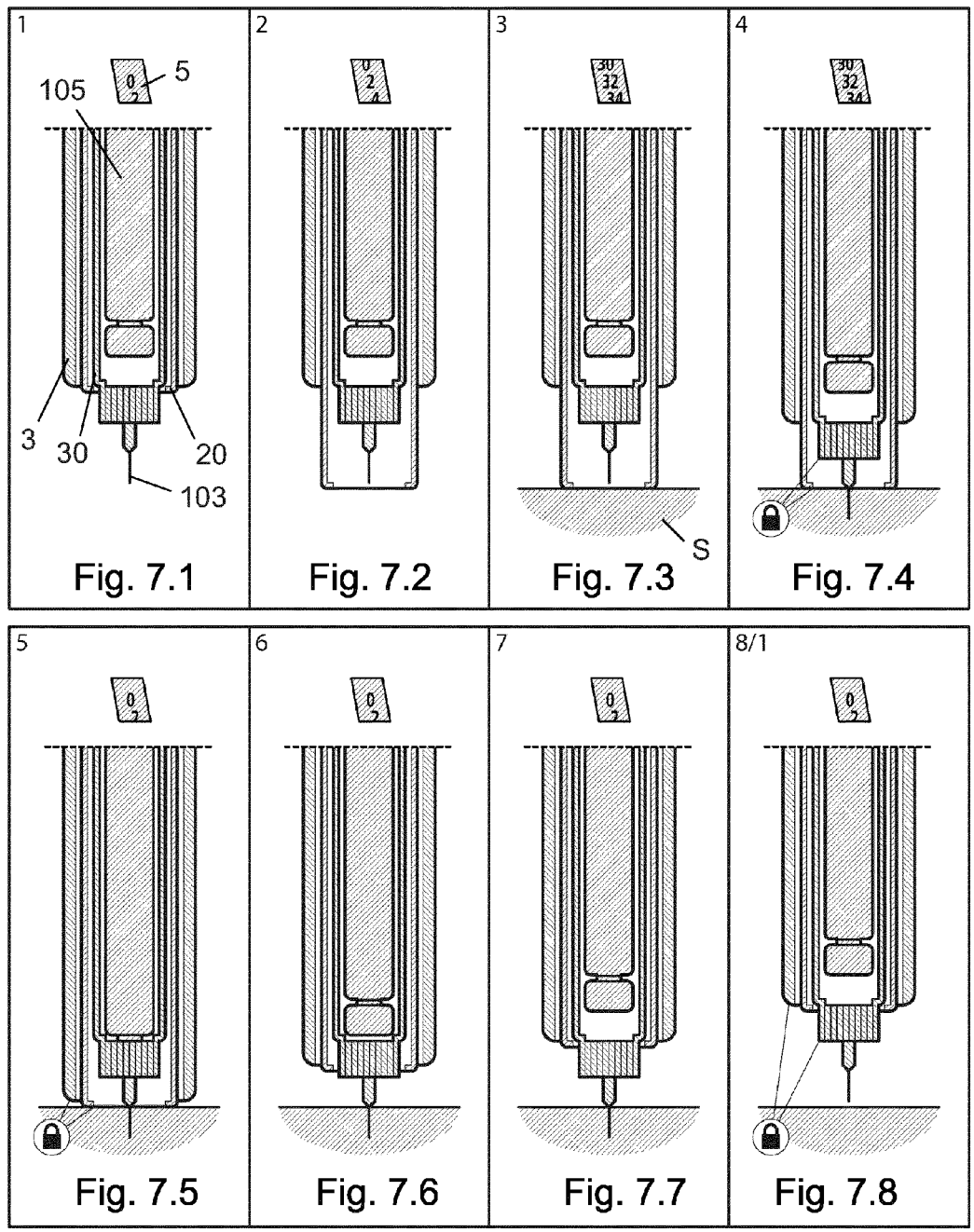
FIG. 7.1-7.8 show a schematic view of the various sequences of performing an injection using the injection device according to the invention.
Figure 8:
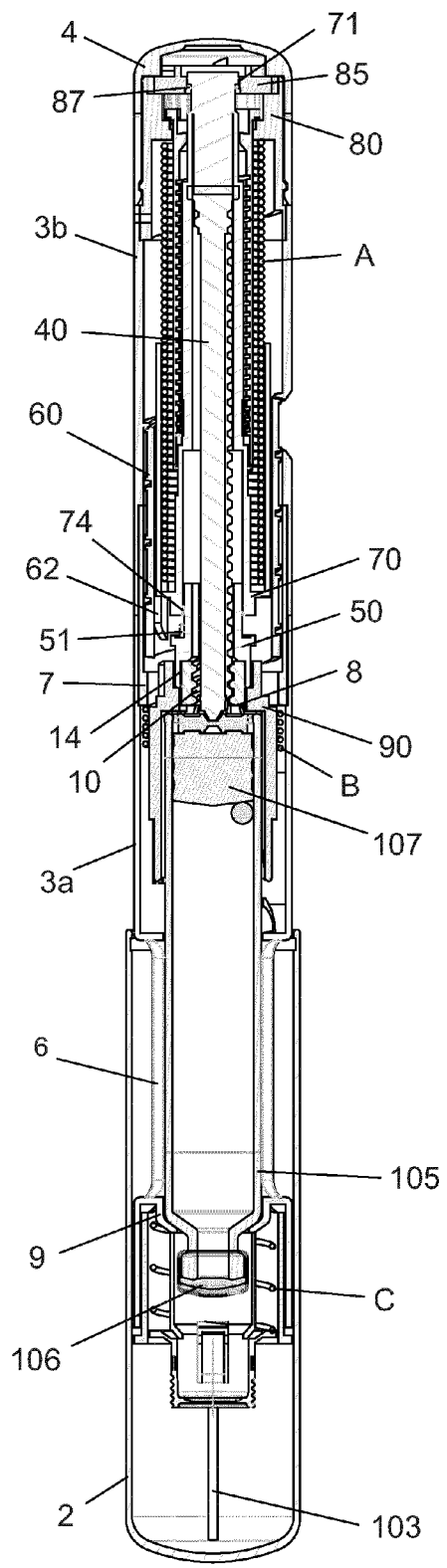
FIG. 8 show a cross sectional view of the injection device according to a first example.

The various sequences of an injection are schematically disclosed in FIG. 7. The details will be further explained in the following.

In FIG. 7.1, the cap 2 has been removed and the injection needle 100 has been connected to the connection means 31 of the needle holder 30. No dose has been dialled as can be seen in the window 5.

In FIG. 7.2 the user dials a dose, and the shield 20 is moved forward to cover the distal end 103 of the injection needle 101.

In FIG. 7.3 the shield 20 is pressed against the skin S of a user.

Figure 15:
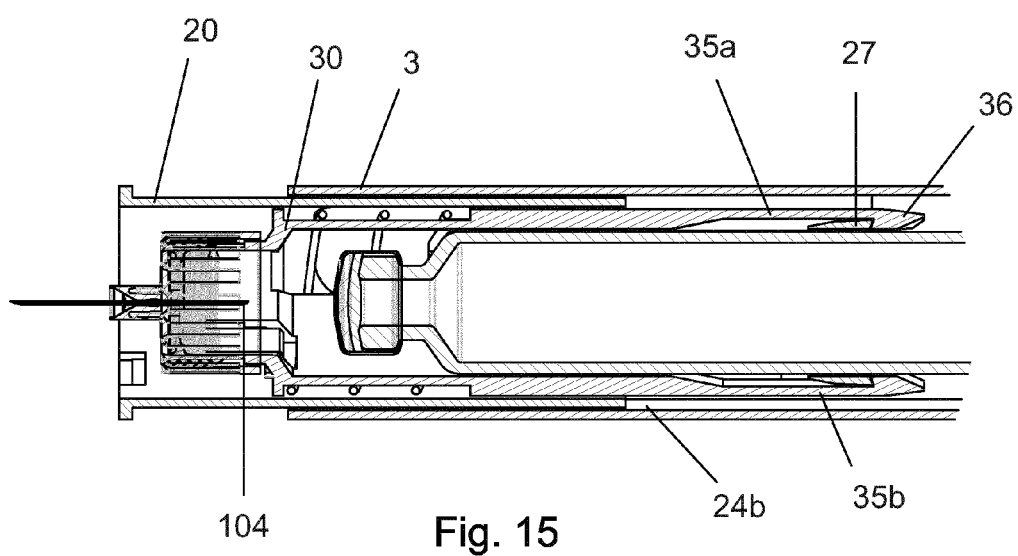
FIG. 15 show a different detailed cross sectional view of the activation mechanism.

In FIG. 7.4, the distal end 103 of the needle cannula 101 has penetrated through the skin S of the user and the needle holder 30 and the shield 20 locks to each other and moves axially together as further disclosed in FIG. 15.

In FIG. 7.5, the proximal end 104 of the needle cannula 101 has penetrated through the septum 106 of the cartridge 105. The injection itself is being executed in this position, indicated by the number "0" appearing in the window 5. Once the scale drum in returned to zero it locks the shield to the housing (via the scale drum).

In FIG. 7.6 the needle holder 30 is forced forward which decouples the proximal end 104 of the needle cannula 101 from the cartridge 105.

In FIG. 7.7 this decoupling is fulfilled and in FIG. 7.8 the needle holder 30 locks to the housing 3.

FIRST EXAMPLE

The operation of the injection device 1 according to a first example will be explained in details in conjunction with the FIGS. 8 to 18.

The mechanics of the injection device 1 is contained in an outer housing 3, which is preferably made from two parts, a distal cartridge holder 3a which is permanently secured to a proximal housing part 3b to form one housing 3. An intermediate part 7 carrying a partition 8 is provided between the cartridge holder 3a and the proximal housing part 3b. Alternatively the housing 3 can be formed as one unitary unit.

As identified before, the distal end of the housing 3 carries a shield 20 and a needle holder 30 whereas the proximal end of the housing 3 carries the dose setting button 4.

The distal cartridge holder part 3a further stores the cartridge 105 which is a conventional cartridge 105 having a septum 106 at its distal end and an axially movable plunger 107 slidable provided at its proximal end. By moving the plunger 107 in the distal direction, the volume of the area between the septum 106 and the plunger 107 is reduced with the volume being pressed out through the needle cannula 101 of the injection needle 100.

The cartridge 105 is axially locked to the housing 3. The proximal end 109 of the cartridge 105 abuts the partition 8 as disclosed in FIG. 10-11 and the shoulders 108 of the cartridge 105 abut inwardly pointing protrusions 9 internally in the housing 3 such that the cartridge 105 cannot slide axially in relation to the housing 3. In order to obtain the tolerances of the cartridge a number of distally pointing fingers 12 can be provided on the partition 8. These fingers 12 preferably has a sloping surface to press against the proximal end 109 of the cartridge 105 as disclosed in FIG. 11. The inwardly pointing protrusions 9 securing the cartridge 105 distally can be provided at a distal end of the opening 6, they could however be provided wherever needed. Alternatively the cartridge 105 can be moulded to the housing 3.

In order to move the plunger 107 forward a drive mechanism is provided which mechanism comprises a threaded piston rod 40 which at its distal end presses against the plunger 107 preferably with a washer 43 provided between the piston rod 40 and the plunger 107.

The intermediate housing part 7 with its internal partition 8 is inrotatable secured to the housing 3 preferably between the two housing parts 3a, 3b. The intermediate housing part 7 could alternatively be moulded as an integral part of the housing 3. The outside thread 41 of the piston rod 40 engages an internal thread 10 provided centrally in the intermediate housing part 7 such that whenever the piston rod 40 is rotated it moves axially in relation to the intermediate housing part 7 a distance determined by the number of revolutions of the piston rod 40 and the pitch of the threads 10, 41.

The piston rod 40 is further provided with an axial stretching track 42 which is engaged by a piston rod guide 50 such that whenever the piston rod guide 50 rotate, the piston rod 40 rotates simultaneously and is screwed forward in the thread connection 10/41.

The needle holder 30 is as disclosed in FIG. 12-13 provided with a number of flexible arms 32 which are pressed outwardly by the inherent force of the flexible arms 32. In this outwardly pointing position, the flexible arms 32 abuts the shield 20 in a pair of grooves 21 provided on a flange 22 of the shield 20 such that the shield 20 is prevented from moving distally relatively to the needle mount 30, as indicated in FIG. 2. In this position a user can mount the injection needle 100 to the connection means 31. When the injection needle 100 is mounted onto the connecting means 31, the flexible arms 32 will bend and be brought into alignment with the outside surface of the connecting means 31 of the needle holder 30 and the shield 20 can slide freely relatively to the needle mount 30 as depictured in FIG. 13.

Figure 10:
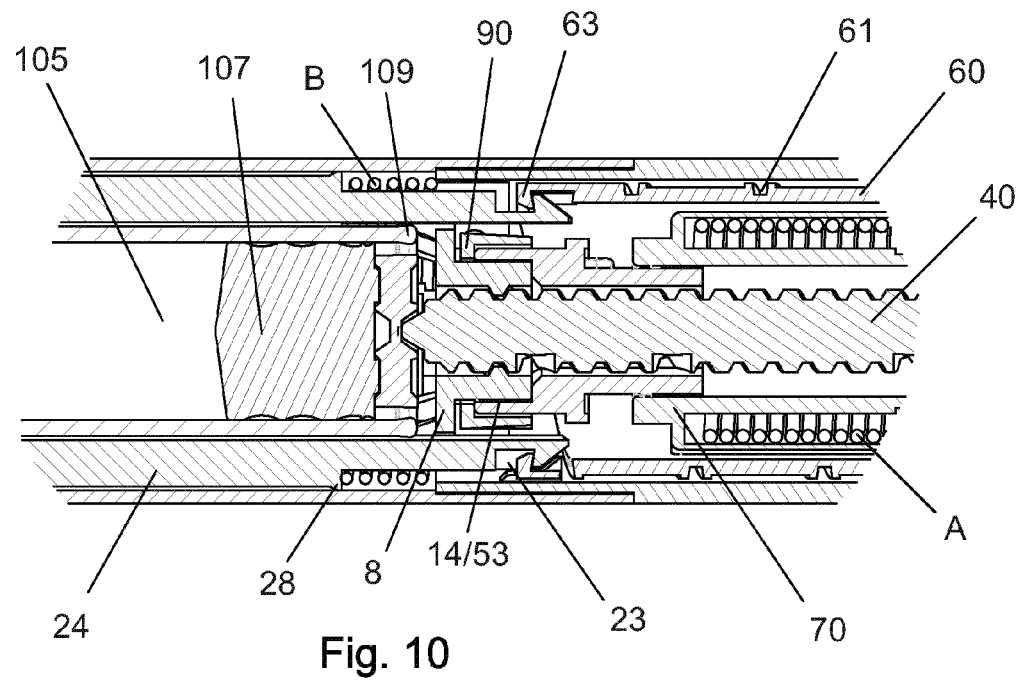
FIG. 10 show a detailed cross sectional view of the engagement between the needle shield and the scale drum.

In order to visually indicate the size of the dose being set by rotating the dose setting button 4 a scale drum 60 is provided. The scale drum 60 is provided with an external thread 61 engaging a similar thread provided internally in the housing 3 as seen in FIG. 10.

The dose setting button 4 engages the drive tube 70 at its proximal end via a ratchet mechanism which is described in details in the not yet published PCT/EP 2013/055403 to Novo Nordisk NS, which is hereby incorporated by reference. This ratchet mechanism as disclosed in FIG. 17 comprises a spring base 80 which is permanently secured to the housing 3 and has an internal toothing engaging the ratchet arms 86 of the ratchet element 85.

The ratchet element 85 is further provided with an internal toothing 87 engaging a similar toothing 71 externally provided on the drive tube 70 such whenever a user rotates the dose setting button 4 to set a dose, the dose setting button 4 rotates the ratchet element 85 and together with it the drive tube 70.

The dose setting button 4 engages directly with the ratchet element 85 which rotates together with the dose setting button 4 both when setting a dose and when lowering the set dose by rotating the dose setting button 4 in the opposite direction. The dose setting button 4 further has an internally provided protrusion which is able to move the ratchet arm 86 out of engagement with the internal toothing of the spring base 80 when the dose is being lowered.

A torsion spring A is provided between the drive tube 70 and the spring base 80, which torsion spring A is strained whenever the drive tube 70 is rotated in the dose setting direction. The spring base 80 could alternatively be a part of the housing 3 in which case the torsion spring A would be encompassed between the housing 3 and the drive tube 70.

Besides the torsion spring A delivering the torsional force to perform the injection, two other springs are provided. A helical spring B applying an axial force is provided between a flange 28 on the shield 20 and the internal partition 8 of the intermediate part 7 of the housing 3 urging the shield 20 in the distal direction and a second axially working helical spring C is provided between a flange 33 provided distally on the needle mount 30 and the housing 3 urging the needle mount 30 in the distal direction. The helical spring C can rest against the distal side of the internal protrusions 9 inside the housing part 3a securing the cartridge 105 as disclosed in FIG. 8.

The drive tube 70 is on an outside surface provided with an axial groove 72 being engaged by a corresponding raised bar 62 internally in the scale drum 60, such that the scale drum 60 follows rotation of the drive tube 70 and can move axially in relation to the drive tube 70. Since the scale drum 60 is threaded to the housing 3 it performs a helical movement whenever rotated. Externally the scale drum 60 is provided with a series of indicia indicating the size of the dose which indicia can be viewed through the window 5 in the housing 3.

Figure 11:
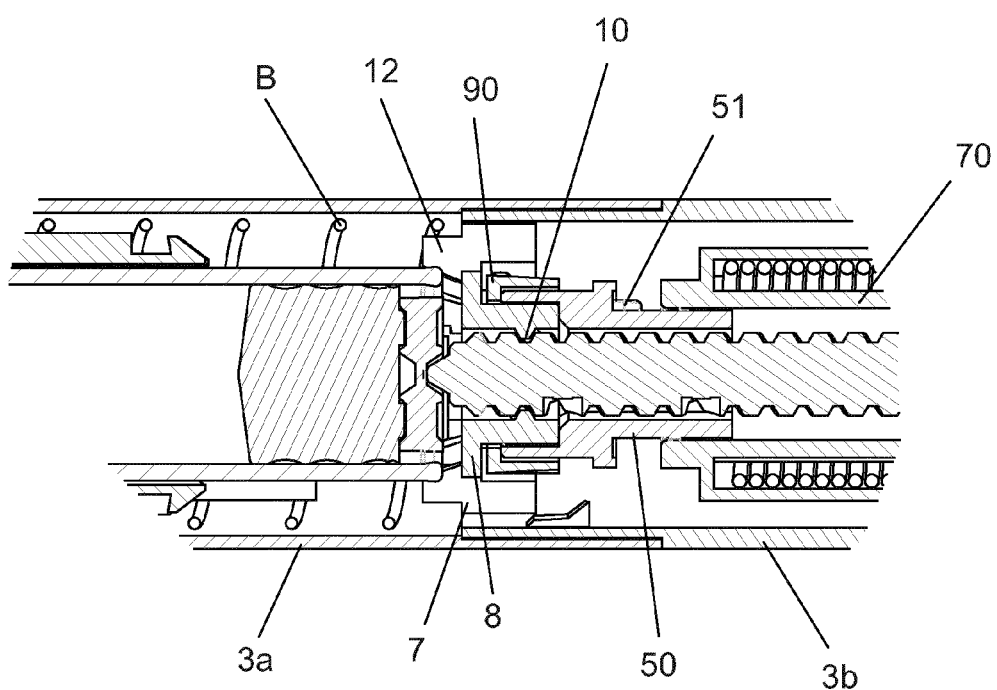
FIG. 11 show a detailed cross sectional view of the needle shield released from the scale drum.

As disclosed in FIGS. 10-11, the distal end the scale drum 60 is internally provided with hooks 63 engaging similar indentations 23 provided proximally on a pair of identical arms 24a,b provided proximally on the shield 20.

The shield 20 is urged in the distal direction by the helical spring B which is encompassed between the partition 8 of the intermediate housing part 7 and the shield 20 thus applying a distally orientated force on the shield 20. The shield 20 is further provided with an axial surface 25 which is guided by a similar axial surface 11 provided along the inspection opening 6 inside the housing 3 such that the shield 20 is guided solely axially without the possibility of rotating relatively to the housing 3.

Whenever the scale drum 60 is in its most distal position, the hooks 63 will engage the indentations 23 on the shield 20 and thus prevent the helical spring B form urging the shield 20 in the distal direction (FIG. 10), however when the scale drum 60 is rotated to set a dose as disclosed in FIG. 11, the indentations 23 are released from the hooks 63 and the shield 20 travels in the distal direction under the force applied by the helical spring B. Thus, when a user dials a dose as depictured in FIG. 4 (arrow D), the shield 20 is released to move in the distal direction to cover the distal end 103 of the needle cannula 101.

End-Of-Content

Figure 17:
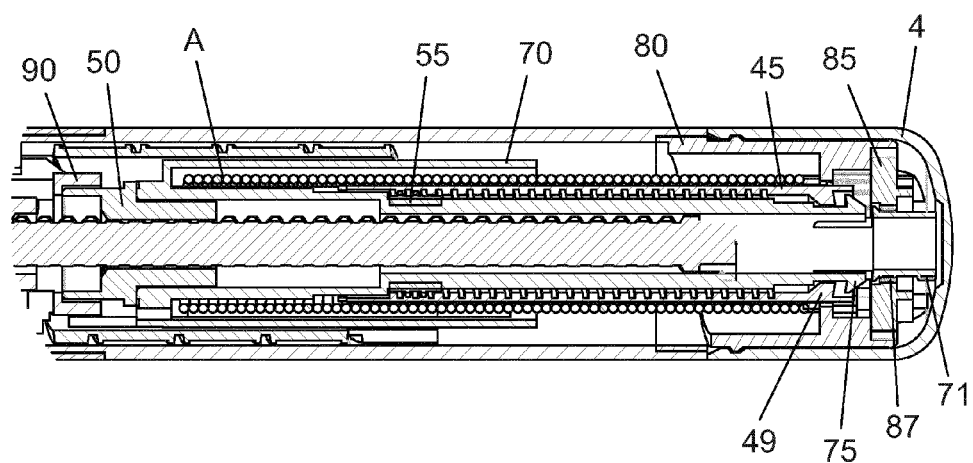
FIG. 17 show a detailed cross sectional view of the proximal end of the injection device.

An end of content mechanism disclosed in FIG. 17 comprises an EOC tube 45 and an EOC ring 55. The EOC ring 55 carries an outside thread 56 which is threaded inside the EOC tube 45 and is axially guided on the drive tube 70 by having an internal protrusion 57 guided in an axial track 73 on the drive tube 70.

Further the EOC tube 45 has an internal flange 49 which is captured by hooks 75 provided on the drive tube 70 allowing the EOC tube 45 to slide a short distance axially in relation to the drive tube 70.

Whenever a dose is set, the drive tube 70 is rotated and the EOC tube 45 is held inrotatable by having teeth 46 engaging similar teeth inside the spring base 80. The EOC ring 55 is thereby dialled up the EOC tube 45 a distance which relates to the size of the set dose. During expelling of the dose, the drive tube 70 is moved axially in relation to the EOC tube 45 as will be explained later, the result being that the distal toothing 47 on the EOC tube engages a similar toothing in the drive tube 70 such that the drive tube 70 and the EOC tube 45 rotates simultaneously during dosing whereby the EOC ring 55 remains in its relative position. The position of the EOC ring 55 in the internal thread of the EOC tube 45 is therefore an expression of the accumulated set doses.

The helical length of the internal thread of the EOC tube is made such that the EOC ring 55 reaches the end of the internal thread of EOC tube 45 when the cartridge 105 is empty, or at least empty for its usable content. At this point the EOC ring 55 abuts the end of the internal thread and prevents further rotation of the drive tube 70, thus no further dose can be set.

The EOC tube 45 can further be provided with teeth 48 engaging similar teeth in the spring base 80 providing dose clicks as the EOC tube 45 rotates with the drive tube 70 during dosing.

Dose Setting

When a user sets a dose by rotating the dose dial button 4 as indicated in FIG. 4, the rotation of the dose setting button 4 causes the ratchet element 85 to also rotate. This rotation is transferred to the drive tube 70 via the toothing 71, 87.

As the drive tube 70 is rotated the torsion spring A encompassed between the spring base 80 and the drive tube 70 is strained. The torsion thereby being built up in the torsion spring A is held by the ratchet arms 86 engaging the internal toothing of the spring base 80. The ratchet arms 86 can be actively released in order to dial down the size of the set dose.

As the drive tube 70 is rotated, the scale drum 60 rotate and move helically thus indicating the size of the set dose in the window 5.

As the scale drum 60 starts to rotate, the hooks 63 of the scale drum 60 moves out of the engagement with the indentations 23 of the shield 20 which is then free to move axially under the influence of the helical spring B. The shield 20 thus moves to a position covering the distal end 103 of the needle cannula 101 as depictured in FIG. 4.

Once the user has set the size of the dose to be injected, the injection device 1 is set and ready to perform an injection.

Activation

Figure 5:
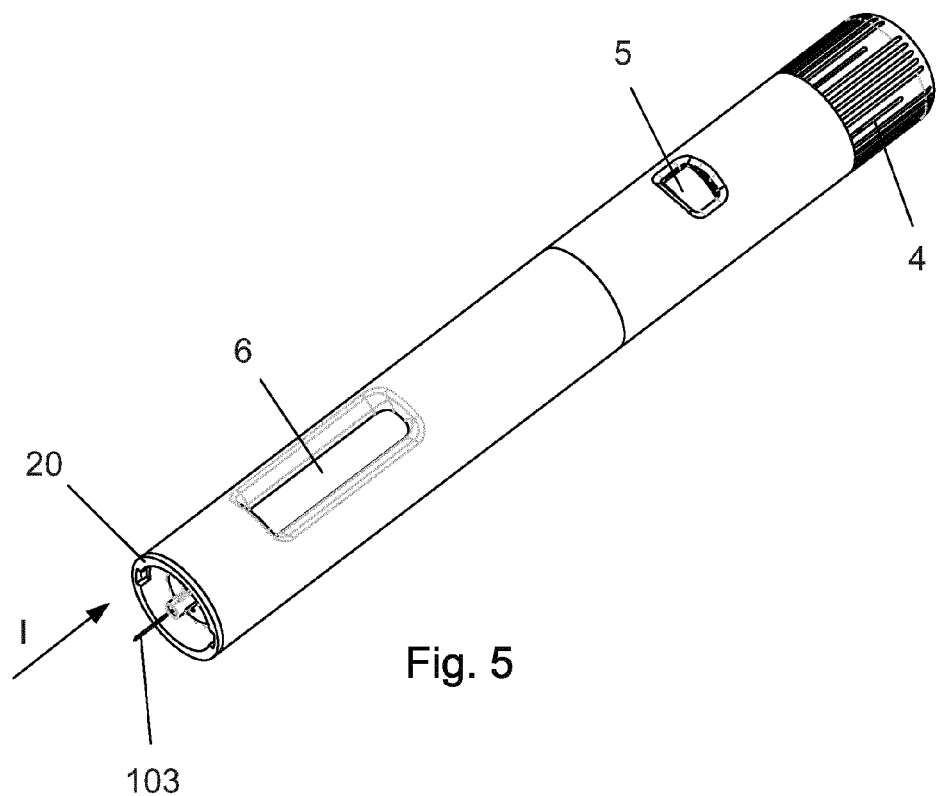
FIG. 5 show a perspective view of the injection device during injection.

In order to release the torque applied to the torsion spring A and thereby to perform an injection, the shield 20 is pressed against the skin of the user as indicated by the arrow I in FIG. 5 which will trigger the injection as explained below.

The needle holder 30 is provided with an identical set of flexible arms 34a,b. These arms 34a,b are blocked in the axial direction by an internal flange 13 provided inside the housing 3 as disclosed in FIG. 14-16.

Figure 16:
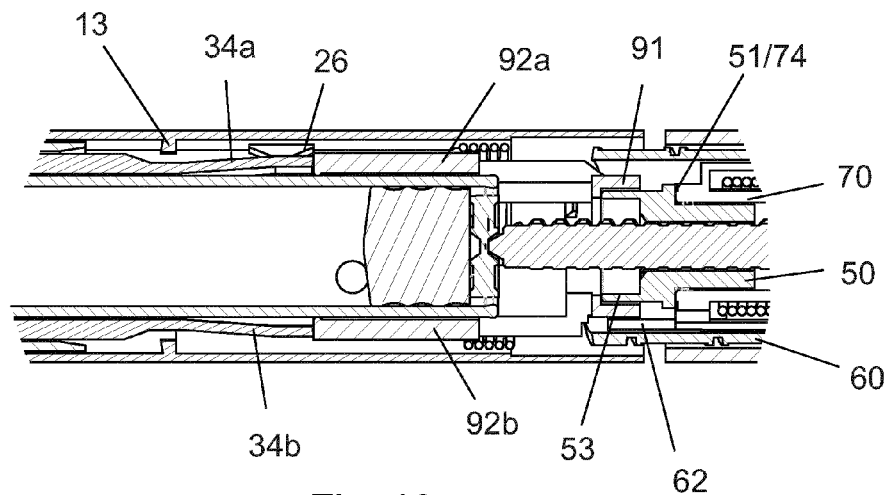
FIG. 16 show a detailed cross sectional view of the activation mechanism upon activation.

Further, the shield 20 is provided with two identical arms 24a,b carrying the indentations 23. These arms 24a,b are each further provided with a protrusion 26 as best seen in FIG. 16. As the shield 20 travels in the proximal direction, this protrusion 26 presses the flexible arms 34a,b inwardly such that the flexible arms 34a,b, can slide under the internal flange 13 of the housing 3 as in FIG. 14 and thus allow the needle shield 30 to slide axially.

The needle holder 30 is further provided with a second pair of identical arms 35a,b. These arms 35a,b carries proximally an extension 36.

The arms 24a,b of the shield 20 each carry a radial protrusion 27 which peripherally follows the outside surface of the cartridge 105. As the shield 20 is moved axially in the proximal direction, the radial protrusions 27 abuts the extension 36 and further axial movement of the shield 20 will thus force the needle holder 30 to move along with the shield 10 in the proximal direction as the arms 34a,b in this position is able to escape under the flange 13.

As both the shield 20 and the needle holder 30 slides in the proximal direction, the proximal end 104 of the needle cannula 101 penetrates through the septum 106 of the cartridge 105 since the cartridge 105 which proximally rest against the partition 8 of the intermediate part 7 is prevented from axial movement.

Dose Release

Once the proximal end 104 of the needle cannula 101 has penetrated through the septum 106 of the cartridge 105 and the distal end 102 has penetrated through the skin of the user, the set dose is released in the following manner.

The axial track of the piston rod 40 is engaged by the piston rod guide 50 as disclosed in FIG. 16. The piston rod guide 50 is further provided with an external toothing 51 (see e.g. FIG. 11) engaging a similar toothing 74 internally in the drive tube 70. The drive tube 70 and the piston rod guide 50 can slide axially relatively such they can shift between a position in which the toothing 74 of the drive tube 70 engages with the toothing 51 of the piston rod guide 50 such that the piston rod guide 50 follows the rotation of the drive tube 70 and a position in which the drive tube 70 and the piston rod guide 50 is disengaged.

Distally, the piston rod guide 50 is engaged by the activator 90.

The activator 90 has a central part 91 which engages the piston rod guide 50 such that the activator 90 can move the piston rod guide 50 axially while the piston rod guide 50 can rotate relatively to the activator 90. Distally, the activator is provided with two identical legs 92a,b.

During activation as the needle holder 30 is moved in the proximal direction by the shield 20, the proximal end of the arms 34a,b abuts the arms 92a,b of the activator 90 and slides the activator 90 in the proximal direction.

This axial movement of the activator 90 pushes the piston rod guide 50 into engagement with the drive tube 70.

The central part 91 of the activator 90 is provided proximally from this wall partition 8 and the legs 92a,b, extend through openings in the partition 8. The partition 8 is further provided with a toothing 14 (FIG. 8) which engages a similar toothing 53 internally in the piston rod guide 50 such that the piston rod guide 50 is prevented from rotation relatively to the partition 8 (and the housing 3) as long as the piston rod guide 50 axially abuts the partition 8.

As the arms 34a,b axially moves the piston rod guide 50 out of engagement with the toothing 14 of the partition 8 and into engagement with the drive tube 70 it also moves the drive tube 70 slightly in the proximal direction. This axial movement of the drive tube 70 moves the proximal toothing 71 of the drive tube 70 out of its engagement with the internal toothing 87 of the ratchet 85 as shown in FIG. 17. As the ratchet element 85 prevents the torque of the torsion spring A from being released, the torsion spring A is now able to rotate the drive tube 70 which rotates with it the piston rod guide 50 and thereby the piston rod 40 to perform an ejection of the liquid drug.

After Dosing

Figure 18:
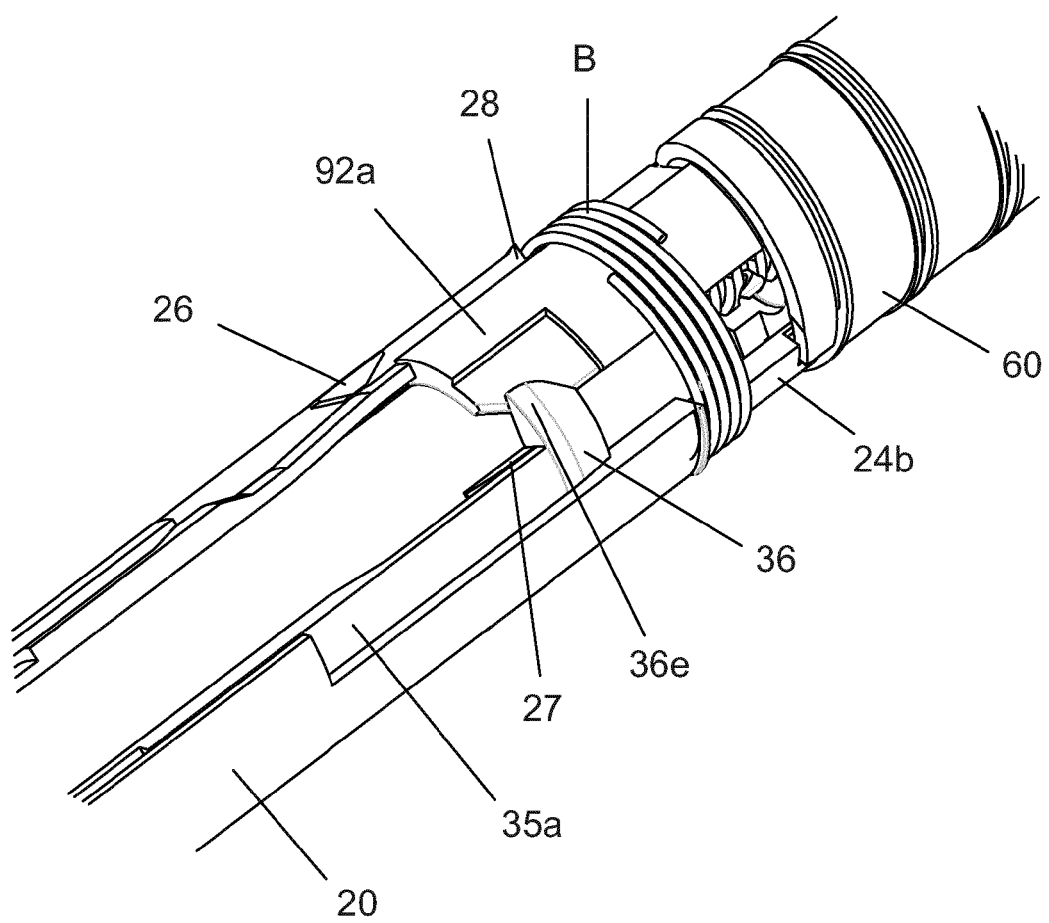
FIG. 18 show a perspective view of the mechanism releasing the needle holder following injection.
Figure 19:
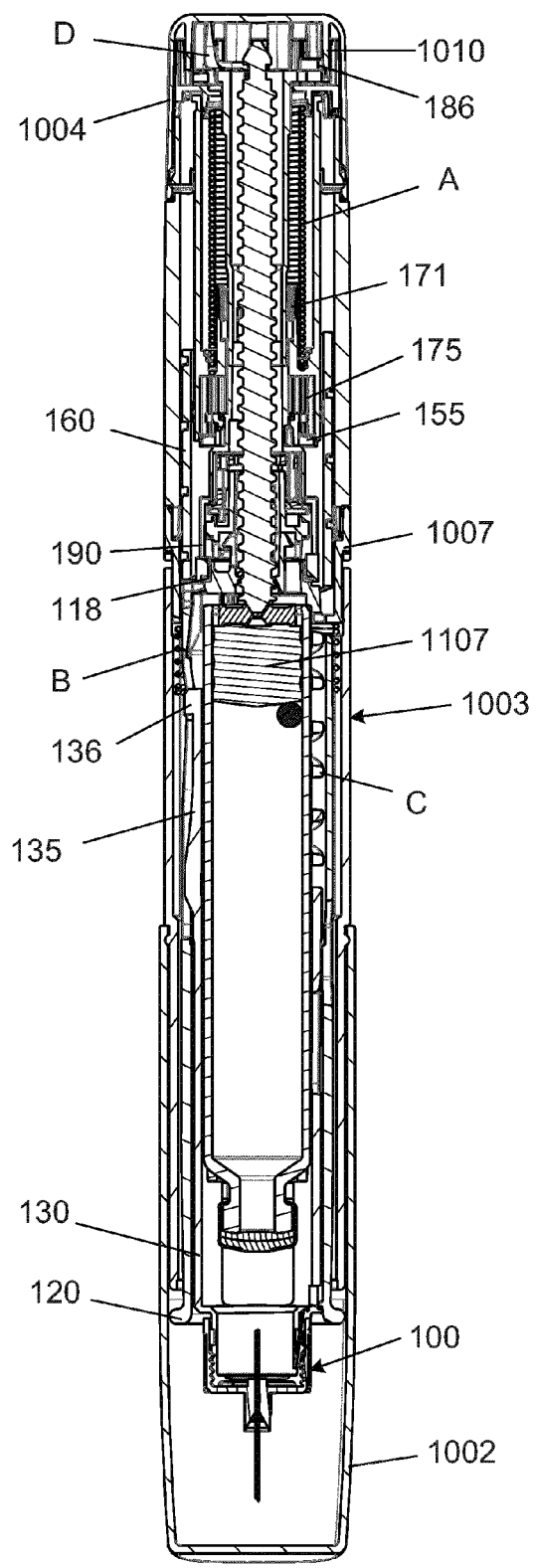
FIG. 19 show a cross sectional view of the injection device according to a second example.

Due to the engagement between the axial groove 72 of the drive tube 70 and the raised bar 62 of the scale drum 60, the scale drum 60 rotates back to its zero position during injection. As the scale drum 60 returns to its zero position as shown in FIG. 18, the raised bar 62 engages an axial surface 93 provided externally on the activator 90. The impact of the scale drum 60 with the activator 90 makes the activator 90 rotate an angle. This rotation makes the arms 92a,b of the activator 90 move under a peripheral extension 36e provided peripheral on the extension 36 which lifts the extension 36 and thereby the proximal end of the arms 35a,b over the radial protrusion 27. In order to enhance this lifting, both the arms 92a,b and the extension 36e are preferably provided with an inclined surface as depictured in FIG. 18. The helical spring C urging an axial force on the needle holder 30 now pushes the needle holder 30 in the distal direction such that the proximal end 104 of the needle cannula 101 is moved out of its engagement with the septum 106 of the cartridge 105. When setting a dose the activator 90 is rotated back to its initial position.

The needle shield 20 is in the zero position locked to the scale drum 60 due to the engagement 63/23 and is thus hindered from moving axially. The result being as shown in FIG. 6, that the needle shield 20 remains in its retracted position and the needle holder 30 moves into its most distal position thereby making it possible for the user to exchange the injection needle 100

SECOND EXAMPLE

A second example which essentially works the same way as the first example is disclosed in the FIGS. 19-26.

Whenever possible the individual elements of the second example are numbered with the same number as in the first example, however, having the number "1" or "10" in front. The same apply for elements performing the same or similar activity.

Figure 9:
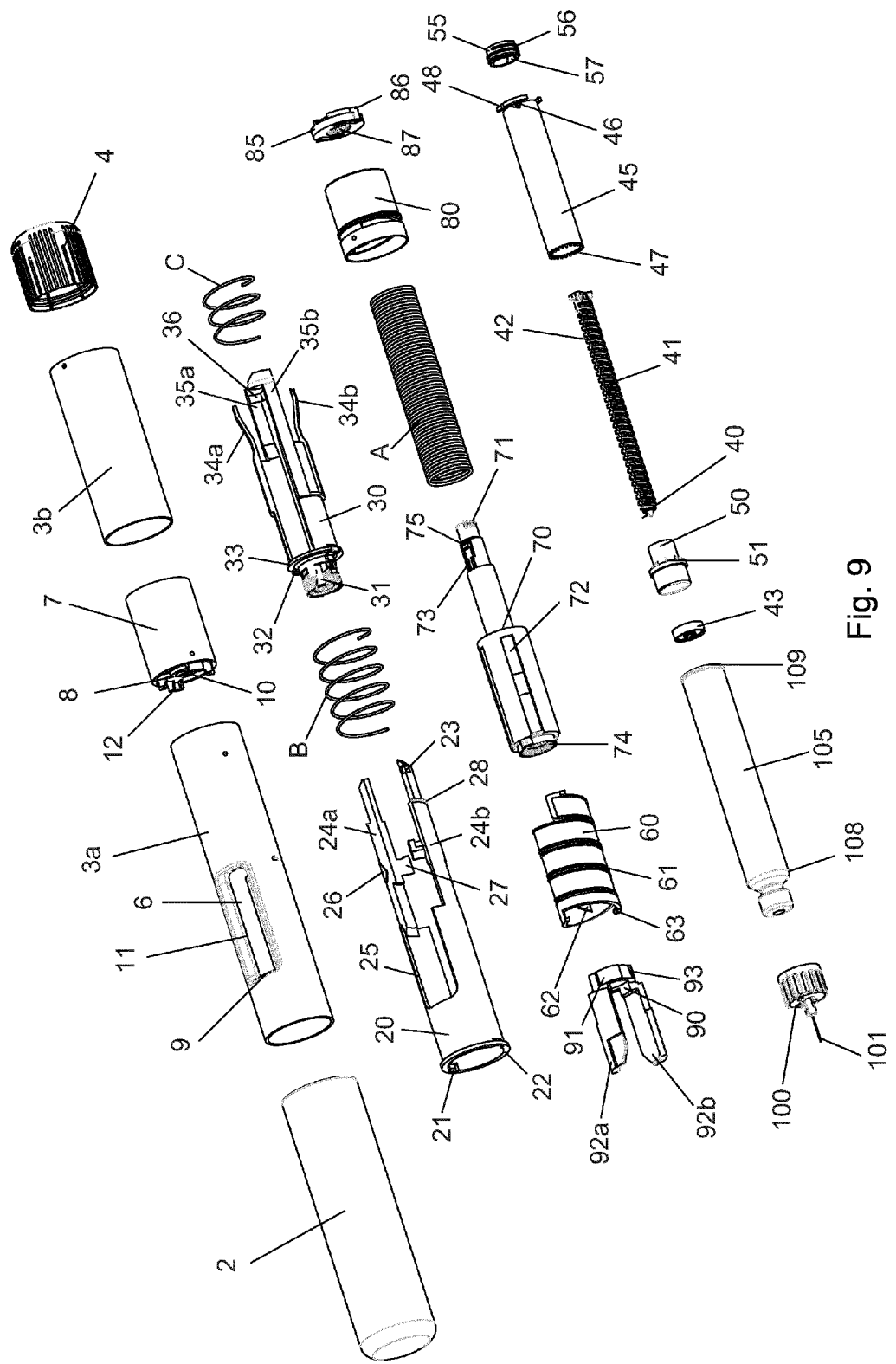
FIG. 9 show an exploded view of the injection device in FIG. 8.

As in FIG. 9 the second example is disclosed in an exploded view in FIG. 20.

As disclosed the housing 1003 is made up from three housing parts; a distal cartridge holder part 1003a holding a cartridge 1105, a proximal housing part 1003b which at its most proximal end is provided with a dose setting button 1004 and an intermediate housing part 1007 connecting the cartridge part 1003*a* and the proximal housing part 1003*b*. The cartridge holder part 1003*a* is further, in the non-use situation, covered by a removable cap 1002.

The intermediate housing part 1007 is further provided with a distal extension 115 which will be explained later and a proximal extension 116. The proximal extension 116 has at its most proximal end a pointer which will appear in the scale window 1005 when the housing 1003 is assembled (best seen in FIG. 21-22). Further, the proximal extension 116 can carry an inwardly pointing thread segment 117 for engaging the external thread 161 on the scale drum 160.

The proximal housing part 1003*a* is provided with two opposite located openings 1006 (one of which is depictured in FIG. 20) into which two frames 111 are press fitted. One or both of these frames 111 are internally provided with a holding mechanism 1009 for holding the neck part 1108 of the cartridge 1105. The proximal end 1109 of the cartridge 1105 is secured against the partition 1008 of the intermediate part 1007 such that the cartridge 1105 is fixed in the housing 1003.

Movable relatively to the housing 1003 is the shield 120 which cover the injection needle during injection and the needle holder 130 having connecting means 131 for securing an injection needle to the needle holder 130. The needle holder 130 is further provided with a flexible arm 132 preventing proximal movement of the shield 120 relatively to the needle holder 130 when no injection needle is mounted on the needle holder 130.

Further, a torsion spring A supplies the torque for performing an injection whereas a compression spring B urges the shield 120 in the distal direction and another compression spring C urges the needle holder 130 in the distal direction.

The torsion spring A is encompassed between the spring base 180 and the drive tube 170. The spring base 180 is permanently fixed to the proximal housing part 1003*b* but could alternatively be moulded as an integral part of the housing 1003.

The compression spring B is encompassed between a flange (or similar) 128 on the shield 120 and the internal partition 1008 of the intermediate housing part 1007. The flange 128 could alternatively be a number of knobs supporting the spring B.

The compression spring C is made from a suitable polymer and is moulded as an integral part of the needle holder 130 and encompassed between the needle holder 130 and the partition 1008 of the intermediate housing part 1007. The partition 1008 can e.g. be provided with a hole 114 for securing the moulded compression spring C.

The intermediate housing part 1007 further has an internal thread 110 through which the piston rod 140 is screwed forward when rotated.

A scale drum 160 for showing the size of the set dose is via an outside thread 161 threaded to the proximal housing part 1003*b* or to the threaded segment 117 of the proximal extension 116 of the intermediate housing part 1007 (or it can be threaded to both as a security measure) such that the scale drum 160 moves helically when rotated. Internally the scale drum 160 is provided with a raised bar 162 axially guided in a corresponding axial groove or the like 172 provided externally on the drive tube 170. The raised bar 162 and axial groove 172 engagement could of cause be vice versa in respect of the parts.

The scale drum 160 is further provided with a hook 163 which holds the shield 120 in its retraced position when the scale drum 160 is in its most distal position i.e. when no dose is set.

The proximally provided dose setting button 1004 is internally rotatable connected to the ratchet element 185 such that rotation of the dose setting button 104 is transformed into rotation of the ratchet element 185. The ratchet element 185 is urged in the distal direction by a compression spring D provided between the proximal end of the ratchet element 185 and the dose setting button 1004. This spring D is preferably moulded integrally with the ratchet element 185 as depictured in FIG. 19. The dose setting button 1004 is further rotatable connected to the housing 1003 such that it can rotate relative to the proximal housing part 1003*b* but not move axially.

The ratchet element 185 is further provided with a ratchet arm 186 which engages an internally toothing 181 provided internally in the spring base 180. The engagement of the ratchet arm 186 with the internal toothing 181 prevents the ratchet element 185 from counter rotating. However, the dose setting button 1004 is internally provided with a protrusion 1010 (FIG. 19) which can move the ratchet arm 186 inwardly when the dose setting button 1004 is rotated oppositely to lower the set dose. In this way the ratchet element 185 can rotate step by step in the opposite direction during dial-down of the dose and under influence of the torsion spring A.

Dose Setting

When setting a dose, as depictured in FIG. 21, the user simply rotates the dose setting button 1004 which in turn rotates the ratchet element 185. Rotation of the ratchet element 185 is transferred to a rotation of the drive tube 170 as the inner toothed surface 174 of the drive tube 170 is in engagement with the outer tooting 187 provided on the ratchet element 185. The rotation of the drive tube 170 strains the torsion spring A. The torque build up in the torsion spring A is held by the engagement of the ratchet arm 186 with the internal toothing 181 of the spring base 180.

The scale drum 160 rotates together with the drive tube 170 such that the user can view the set dose through the window 105 provided in the proximal housing part 103*b*.

Once the scale drum 160 is rotated away from its "zero" position the hook 163 is rotated out of its engagement with the indentation 123 (see FIG. 23-26) provided on the shield 120 which is then urged distally by the compression spring B.

The needle holder 130 is further urged forward by the compression spring C such that the back-end of the injection needle is maintained outside the septum 1106 of the cartridge 1105 when not injecting.

Injecting

In order to inject the set dose, the distal end of the shield 120 is pressed against the skin of the user.

When the user starts to press the shield 120 against the skin, the front-end 103 of the injection needle 100 penetrates through the skin while the back-end 104 of the injection needle is out of contact with the septum 1106 of the cartridge 1105 as the needle holder 130 is in its distal position. In this position, the needle holder 130 is prevented from moving proximally by the engagement of the protrusion 134*a* carried on the flexible arm 134 against an inwardly pointing protrusion 113 (see FIG. 20) provided on the frame 111.

However, once the front-end 103 of the injection needle 100 is fully inserted into the skin as depictured in FIG. 7.4, the shield 120 will force the protrusion 134*a* out of its engagement with the inwardly pointing protrusions 113 of the frame 111 since the vertical protrusion 134*b* of the flexible arm 134 is guided in a track 126 in the shield 120. The shape of this track 126 moves the protrusion 134*a* (via 134*b*) out of its engagement with the inwardly pointing protrusion 113 on the frame 111 where after the shield 120 and the needle holder 130 move axially together.

Figure 23:
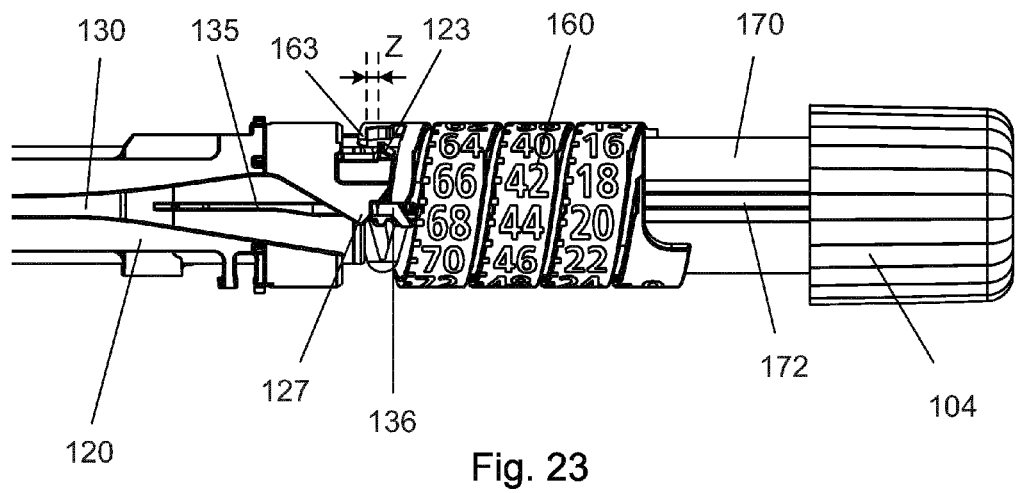
FIG. 23 show a side view of the interior of the injection device of the FIGS. 19-20 with the needle holder locked to the needle shield.
Figure 24:
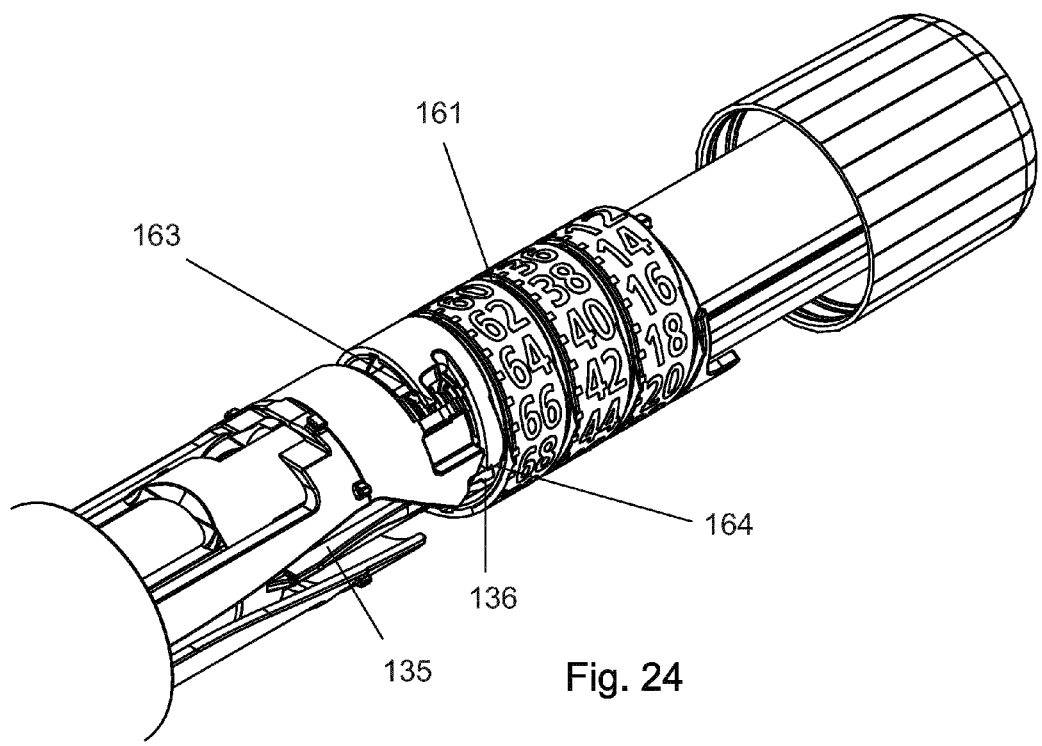
FIG. 24 show a perspective view of FIG. 22.

The shield 120 and needle holder 130 moves together since the protrusion 136 provided on the arm 135 locks to the hook 127 proximally provided on the shield 120. Axial movement of the shield 120 is thus transferred to the needle holder 130. This is best seen in FIG. 23-24 which depictures the situation occurring during dose expelling and just before the scale drum 160 reaches its zero position. The hook 127 engages the protrusion 136 thus transferring axial movement of the shield 120 to axial movement of the needle holder 130.

The arm 135 carrying the protrusion 136 is guided into position by the curved wall 129 leading up to the hook 127. Oppositely the arm 135 is supported by the curved extension 115 on the intermediate housing part 1007.

When the shield 120 is fully retracted, as depictured in FIG. 7.5, the back-end 104 of the injection needle 100 has penetrated through the septum 1106 and into the cartridge 1105 and the release of the dose will be activated.

Dose Release

Proximally on the needled holder 130 one or more release arms 137 are provided. These release arms 137 extent parallel with the flexible arm 135. When the shield 120 and the needle holder 130 is in their proximal position, the release arms 137 moves the clutch 190 as depictured in FIG. 22. This brings the external toothing 191 on the clutch 190 into engagement with a similar toothing 174 provided internally in the drive tube 170 such that the drive tube 170 and the clutch 190 rotate together.

During dose setting, the ratchet element 185 rotates the drive tube 170 via the engagement of the externally provided toothing 187 engaging the toothing 174 internally in the drive tube 170, see FIG. 21.

Further, during dose setting, the ratchet element 185 rotate together with the dose setting button 1004, but during dosing both the dose setting button 1004 and the ratchet element 185 remains non-rotatable. When the clutch 190 is moved proximally by the arms 137, the ratchet element 185 is also moved proximally against the bias of a proximally moulded spring arm D provided proximally on the ratchet element 185 and resting against an inside surface of the dose setting button 1004.

This proximal movement of the ratchet element 185 releases the coupling between the toothing 174 of the drive tube 170 and the toothing 187 provided on the ratchet element 185 such that the drive tube 170 is free to rotate under influence of the torque of the torsion spring A.

The rotation of the drive tube 170 is transferred to a rotation of the clutch 190 by the coupling between the internal toothing 174 on the drive tube 170 and the toothing 191 externally and proximally on the clutch 190.

I.e. when the clutch 190 slides proximally (moves from the position in FIG. 21 to the position of FIG. 22) the toothing 174 of the drive tube 170 releases the engagement with the toothing 187 of the ratchet element 185 and couples to the toothing 191 of the clutch 190.

A further toothing 171 is also provided internally in drive tube 170, which toothing 171 operates against click arms 188 provided externally on the ratchet element 185 to provide dose clicks during injection i.e. when the drive tube 170 rotate relatively to the ratchet element 185.

Please note that in the FIGS. 21-22 part of the clutch 190 is not visible due to the cross sectional view. However, the clutch 190 is fully depictured in FIG. 19

Further, the rotation of the clutch 190 is transferred to a rotation of the piston rod guide 150 as the toothed outer surface 151 of the piston rod guide 150 is in engagement with the internal toothing 194 of the clutch 190 when the clutch 190 is moved proximally during dosing as disclosed in FIG. 22.

As seen in FIG. 21-22 this internal toothing 194 of the clutch 190 is in engagement with a toothing 118 on the intermediate housing member 1007 when the injection device is not activated.

The rotation of the piston rod guide 150 is transferred to a rotation of the piston rod 140 as the piston rod guide 150 engages a longitudinal track in the piston rod 140.

Pressure Relief

The pressure relief mechanism is similar to the one disclosed in EP 12-188471 by Novo Nordisk NS and serves the purpose of allowing axial movement of the rubber plunger 1107 of the cartridge 1105 and thus also of the piston rod 140. Such axial movement of the rubber plunger occurs e.g. as a result of temperature variations.

The pressure relief mechanism comprises of the clutch 190, the piston rod guide 150, a click element 165 and a leaf spring E.

If the liquid drug inside the cartridge 1105 expands due to increasing temperatures, the piston rod 140 will be forced proximally by the rubber plunger 1107 inside the cartridge 1105, which will push the piston rod foot 143 and thus the piston rod 140 proximally. This will generate a rotation of the piston rod 140 as the piston rod 140 is threaded to the thread 1008 of the intermediate part 1007.

This will force the piston rod guide 150 to rotate as the piston rod guide 150 is keyed to the piston rod 140.

The click element 165 is externally provided with a plurality of click fingers 166 which operates in a toothing 195 provided internally in the clutch 190. This toothing 195 is adapted to prevent rotation of the click element 165 in one direction and adapted to have reluctance to rotation in the opposite direction (due to the inherent outwardly flexibility of the click fingers 166).

The direction having the reluctance is the one being used when the piston rod 140 move proximally as the temperature rises.

The leaf spring E is encompassed between the piston rod guide 150 and the click element 155 such that one leg of the leaf spring D is attached to the piston rod guide 150 and the other leg is attached to the click element 165 thus a torque will be introduced in the leaf spring E when the piston rod guide 150 and the click element 165 rotate relative to each other independently of the direction of this rotation.

When the piston rod 140 move proximately and the piston rod guide 150 rotates, the leaf spring E is tighten until the rotational reluctance of the click element 165 is overcome where after the click fingers 166 will move to the subsequent teeth of the toothing 195. The result being that the piston rod guide 150 can perform an unlimited rotation in the expanding direction.

When the temperature decreases and the rubber plunger move distally the torque introduced in the leaf spring E will rotate the piston rod guide 150 since the toothing 195 prevents the click element 165 from rotation in this opposite direction. The result being that the piston rod 140 is rotated forward.

End-Of-Content

The End-of-Content mechanism is a so-called non-axial movable cycloid End-of-Content mechanism which is disclosed in details in EP 13-153628 by Novo Nordisk NS.

The End-of-Content mechanism comprises an End-of-Content ring 155 which internally rides on an outside surface of the clutch 190 and externally is connected to a toothed ring 175 provided inside drive tube 170 such that the End-of-Content ring 155 rotate when the drive tube 170 is rotated relatively to the clutch 190.

During dose setting the drive tube 170 is rotated and the clutch 190 is static thus the End-on-Content ring 155 is rotated. During dosing the drive tube 170 and the clutch 190 rotate together thus maintaining the End-of-Content ring 155 in the same relative position.

Due to the cycloid gearing the End-of-Content ring 155 is rotated a greater angle for each angular rotation of the drive tube 170 thereby counting the rotational movement of the drive tube 170. The total allowable angular movement of the End-of-Content ring 155 is predetermined such that the End-of-Content ring 155 encounters a stop just before the injectable content of the cartridge 1105 has been set. Once the End-of-Content ring 155 reaches its stop, the drive tube 170 cannot be rotated further thus no further dose can be set.

The End-of-Content mechanism thereby counting the accumulated set and ejected doses and stopping further dose setting when this accumulated value equals the initial injectable amount of liquid drug in the cartridge 1105.

After Dosing

Following dose release the user removes the shield 120 from the skin as disclosed in FIG. 7.8.

This makes the needle holder 130 move distally under the influence of the compression spring C as depictured in FIG. 23-24 such that the back-end 104 of the attached pen-needle 100 is pulled out of the septum 1106 of the cartridge 1105.

As the scale drum 160 approaches its zero position as depictured in FIG. 23-24, the surface 164 on the scale drum 160 encounters the protrusion 136 and pushes it out of its engagement with the hook 127 such that the needle holder 130 can move distally independently of the shield 120.

To make sure that the needle holder 130 do not return until the shield 120 has been fully removed from the skin of the user, the protrusion 136 is hindered by axial movement by the supporting surface 115 until the shield 120 has moved a little distance in the distal direction (the distance is indicated by the arrow Z in FIG. 23). The axial movement being the axial distance Z between hook 163 and indentation 123 seen in FIG. 23. Only when the shield 120 has moved to the hooked position (FIG. 25) is the distance to the supporting surface 115 sufficient to allow the protrusion 136 to be fully released where after the needle holder 130 returns to its extended position.

Figure 25:
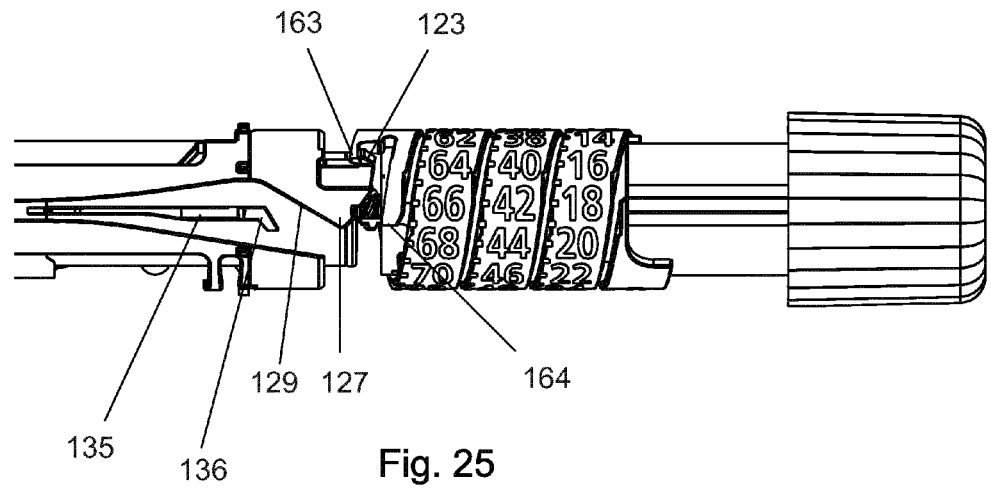
FIG. 25 show a side view of the interior of the injection device of the FIGS. 19-20 with the needle holder released from the needle shield and the needle shield locked to the scale drum.
Figure 26:
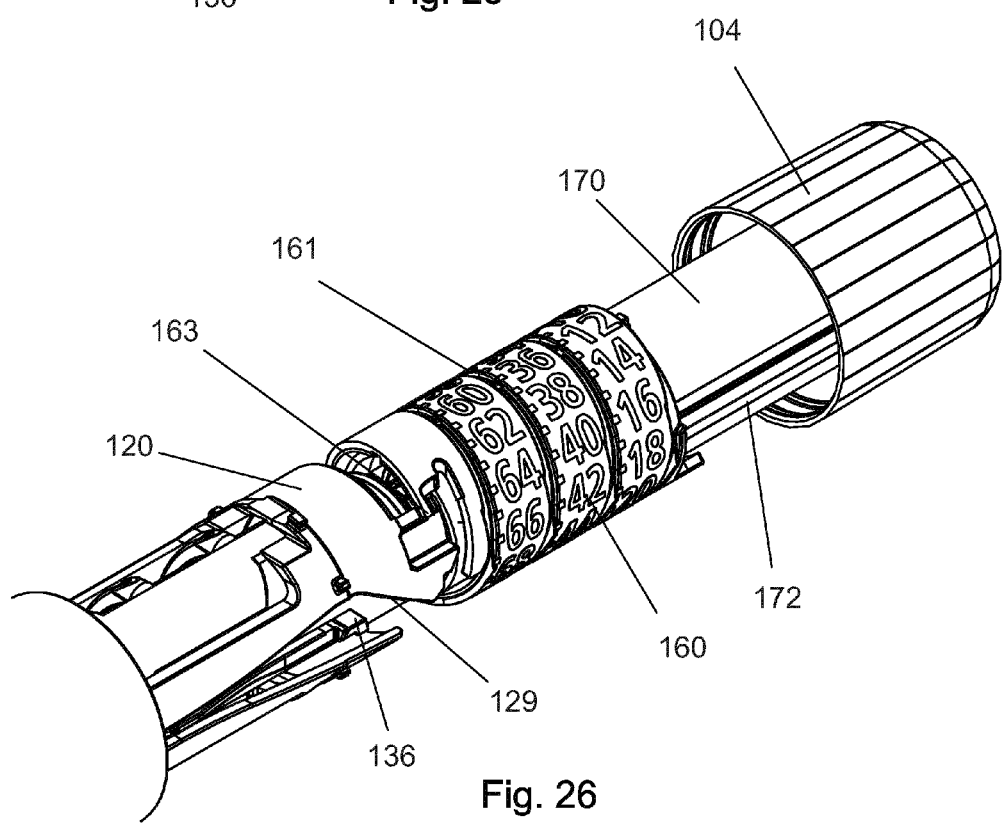
FIG. 26 show a perspective view of FIG. 24.

Also following injection, the hook 163 provided on the scale drum 160 once again engages the indentation 123 provided proximately on the shield 120 thus preventing further axial movement of the shield 120 as depictured in FIG. 24-25.

This mechanism is further disclosed in European patent application No.: EP 13-170422 by Novo Nordisk NS.

Some preferred embodiments have been shown in the foregoing, but it should be stressed that the invention is not limited to these, but may be embodied in other ways within the subject matter defined in the following claims

The invention claimed is:

1. A spring driven drug delivery device for delivering set doses of a liquid drug comprising;
    a housing securing a cartridge sealed at one end by a pierceable septum, containing the liquid drug and which cartridge is axially fixated to the housing,
    a dose setting arrangement for setting the size of the dose to be delivered,
    a torque spring drive mechanism for automatically driving the set dose out from the cartridge through an exchangeable injection needle, having a distal front-end and a proximal back-end, mountable to the drug delivery device, the torque spring drive mechanism comprising a piston rod which is axially displaceable through engagement with a rotational piston rod guide rotational under the influence of a torsion spring,
    a telescopically movable needle shield for covering a distal end of the exchangeable injection needle being attached in an extended position and which needle shield when axially moved to a retracted position triggers release of at least a portion of the torque of the torsion spring in order to perform an ejection of the liquid drug, and wherein
    during injection, a needle holder for carrying the exchangeable injection needle is axially movable relatively to both the housing and to the needle shields the needle holder being axially slidably mounted in the housing such that the needle holder carrying the injection needle and the housing carrying the cartridge can be moved axially in relation to each other such that the proximal back-end of the injection needle can be moved into and out of engagement with the septum of the cartridge.

2. The spring driven drug delivery device according to claim 1, wherein the torsion spring is encompassed between the housing and the piston rod guide.

3. The spring driven drug delivery device according to claim 2, wherein a drive tube is rotatable during dose expelling and which drive tube rotates the piston rod guide.

4. The spring driven drug delivery device according to claim 3, wherein a clutch couples the drive tube to the piston rod guide during dose expelling.

5. The spring driven drug delivery device according to claim 4, wherein the clutch is movable between a first position in which the clutch is rotational locked to the housing and a second position in which the clutch is rotational released from the housing and rotational coupled to the drive tube and to the piston rod guide such that the torque of the torsion spring is transformed into a rotation of the piston rod guide in the second position.

6. The spring driven drug delivery device according to claim 1, wherein the needle shield is movable from the retracted position to the extended position under the influence of a helical compression spring provided between the housing and the needle shield upon activation of a dose setting button of the dose setting arrangement.

7. The spring driven drug delivery device according to claim 6, wherein the dose setting arrangement upon rotation of the dose setting button is adapted to rotate a scale drum which is threadedly engaged with the housing to perform a helical movement and which scale drum engages and locks the needle shield when in a zero position.

8. The spring driven drug delivery device according to claim 7, wherein hooks formed on the needle shield engages cooperating hooks provided on the scale drum in the retracted position.

9. The spring driven drug delivery device according to claim 1, wherein the needle shield is slidable on an outside surface of the needle holder and which needle holder is provided with a number of flexible arms projecting from an outside surface of the needle holder and engaging the needle shield.

10. The spring driven drug delivery device according to claim 1, wherein the needle shield when moved from its extended position to its retracted position abuts and moves the needle holder axially.

11. The spring driven drug delivery device according to claim 10, wherein the needle shield has a number of protrusions which engages the needle holder to move the needle holder axially.

12. The spring driven drug delivery device according to claim 11, wherein one or more protrusion carried by proximate extending arms provided on the needle holder engages the protrusions of the needle shield.

13. The spring driven drug delivery device according to claim 10, wherein the injection needle moves axially together with the needle holder such that the proximal back-end of the injection needle penetrates the pierceable septum in the cartridge thereby allowing the liquid drug to flow through the injection needle.

14. The spring driven drug delivery device according to claim 5, wherein an axial movement of the needle holder moves the clutch from its first position to its second position thereby activating the release of the torsion spring to drive the torque spring drive mechanism.

15. The spring driven drug delivery device according to claim 8, wherein the scale drum rotates back to its zero position during expelling of the set dose under influence of the torsion spring.

16. The spring driven drug delivery device according to claim 15, wherein the scale drum when it reaches its zero position following injection releases the needle holder such that the needle holder move axially in the distal direction under influence of a helical compression spring provided between the needle holder and the housing.

17. The spring driven drug delivery device according to claim 16, wherein the scale drum abuts a protrusion of the needle holder to release the needle holder to move axially.

\* \* \* \* \*

UNITED STATES PATENT AND TRADEMARK OFFICE
CERTIFICATE OF CORRECTION

PATENT NO. : 9,901,680 B2  
APPLICATION NO. : 14/408840  
DATED : February 27, 2018  
INVENTOR(S) : Simon Roervig et al.

Page 1 of 1

It is certified that error appears in the above-identified patent and that said Letters Patent is hereby corrected as shown below:

In the Claims

At Column 20, Claim number 1, Line number 27, please replace:
"shields"
With:
"shield,"

Signed and Sealed this
Sixth Day of November, 2018

Andrei Iancu
*Director of the United States Patent and Trademark Office*